US011529480B2

(12) United States Patent
Meyer et al.

(10) Patent No.: US 11,529,480 B2
(45) Date of Patent: *Dec. 20, 2022

(54) OSCILLATING POSITIVE EXPIRATORY PRESSURE DEVICE

(71) Applicant: Trudell Medical International, London (CA)

(72) Inventors: Adam Meyer, London (CA); Noel Gulka, London (CA); James Schmidt, London (CA)

(73) Assignee: Trudell Medical International, London (CA)

( * ) Notice: Subject to any disclaimer, the term of this patent is extended or adjusted under 35 U.S.C. 154(b) by 290 days.

This patent is subject to a terminal disclaimer.

(21) Appl. No.: 16/903,685

(22) Filed: Jun. 17, 2020

(65) Prior Publication Data

US 2020/0376214 A1 Dec. 3, 2020

Related U.S. Application Data

(63) Continuation of application No. 15/919,790, filed on Mar. 13, 2018, now Pat. No. 10,722,668, which is a
(Continued)

(51) Int. Cl.
*A61M 16/00* (2006.01)
*A61M 16/08* (2006.01)
(Continued)

(52) U.S. Cl.
CPC ........ *A61M 16/0057* (2013.01); *A61M 11/02* (2013.01); *A61M 15/00* (2013.01);
(Continued)

(58) Field of Classification Search
CPC .......................... A61M 16/208; A61M 11/06; A61M 15/0098; A61M 16/20; A61M 16/14;
(Continued)

(56) References Cited

U.S. PATENT DOCUMENTS 393,869 A 12/1888 Warren
938,808 A 11/1909 Yount
(Continued)

FOREIGN PATENT DOCUMENTS

EP 0 372 148 A1 6/1990
EP 0 678 306 A2 10/1995
(Continued)

OTHER PUBLICATIONS

U.S. Appl. No. 14/674,494, filed Mar. 31, 2015, Meyer et al.
(Continued)

*Primary Examiner* — Steven O Douglas
(74) *Attorney, Agent, or Firm* — Crowell & Moring LLP

(57) ABSTRACT

An oscillating positive expiratory pressure device comprising a housing enclosing at least one chamber, a chamber inlet configured to receive exhaled air into the at least one chamber, and a chamber outlet configured to permit exhaled air to exit the at least one chamber. A channel is positioned in an exhalation flow path between the chamber inlet and the chamber outlet, with the channel being movably connected to a chamber of the at least one chamber. An air flow regulator is movable with respect to the channel between a first position, where the flow of air through the channel is restricted and a second position, where the flow of air through the channel is less restricted, the air flow regulator being configured to repeatedly move between the first position and the second position in response to a flow of exhaled air.

20 Claims, 30 Drawing Sheets

Related U.S. Application Data continuation of application No. 14/946,409, filed on Nov. 19, 2015, now Pat. No. 9,950,128, which is a continuation of application No. 13/920,250, filed on Jun. 18, 2013, now Pat. No. 9,220,855, which is a continuation of application No. 12/711,032, filed on Feb. 23, 2010, now Pat. No. 8,485,179.

(60) Provisional application No. 61/181,200, filed on May 26, 2009, provisional application No. 61/154,661, filed on Feb. 23, 2009.

(51) Int. Cl.
*A61M 15/00* (2006.01)
*A61M 16/14* (2006.01)
*A61M 11/02* (2006.01)
*A61M 16/20* (2006.01)
*A61M 11/06* (2006.01)

(52) U.S. Cl.
CPC ........ *A61M 16/00* (2013.01); *A61M 16/0006* (2014.02); *A61M 16/0866* (2014.02); *A61M 16/14* (2013.01); *A61M 16/20* (2013.01); *A61M 11/06* (2013.01); *A61M 15/0098* (2014.02); *A61M 16/208* (2013.01)

(58) Field of Classification Search
CPC ...... A61M 16/00; A61M 15/00; A61M 11/02; A61M 16/0866; A61M 16/0006; A61M 16/0057
See application file for complete search history.

(56) References Cited

U.S. PATENT DOCUMENTS

| | | |
|---|---|---|
| 2,670,739 A | 3/1954 | NcNeill |
| 2,918,917 A | 12/1959 | Emerson |
| 3,710,780 A | 1/1973 | Milch |
| 3,908,987 A | 9/1975 | Boehringer |
| 4,054,134 A | 10/1977 | Kritzer |
| 4,062,358 A | 12/1977 | Kritzer |
| 4,182,366 A | 1/1980 | Boehringer |
| 4,198,969 A | 4/1980 | Virag |
| 4,221,381 A | 9/1980 | Ericson |
| 4,226,233 A | 10/1980 | Kritzer |
| 4,231,375 A | 11/1980 | Boehringer et al. |
| 4,267,832 A | 5/1981 | Hakkinen |
| 4,275,722 A | 6/1981 | Sorensen |
| 4,298,023 A | 11/1981 | McGinnis |
| 4,327,740 A | 5/1982 | Shuman |
| 4,403,616 A | 9/1983 | King |
| 4,436,090 A | 3/1984 | Darling |
| 4,470,412 A | 9/1984 | Nowacki et al. |
| 4,601,465 A | 7/1986 | Roy |
| 4,611,591 A | 9/1986 | Inui et al. |
| 4,635,631 A | 1/1987 | Izumi |
| 4,651,731 A | 3/1987 | Vicenzi et al. |
| 4,739,987 A | 4/1988 | Nicholson |
| 4,770,413 A | 9/1988 | Green |
| 4,951,661 A | 8/1990 | Sladek |
| 4,973,047 A | 11/1990 | Norell |
| 4,981,295 A | 1/1991 | Belman et al. |
| 5,018,517 A | 5/1991 | Liardet |
| 5,042,467 A | 8/1991 | Foley |
| 5,065,746 A | 11/1991 | Steen |
| 5,193,529 A | 3/1993 | Labaere |
| 5,345,930 A | 9/1994 | Cardinal et al. |
| 5,372,128 A | 12/1994 | Haber et al. |
| 5,381,789 A | 1/1995 | Marquardt |
| 5,451,190 A | 9/1995 | Liardet |
| 5,479,920 A | 1/1996 | Piper et al. |
| 5,540,220 A | 7/1996 | Gropper et al. |
| 5,569,122 A | 10/1996 | Cegla |
| 5,570,682 A | 11/1996 | Johnson |
| 5,598,839 A | 2/1997 | Niles et al. |
| 5,613,489 A | 3/1997 | Miller |
| 5,645,049 A | 7/1997 | Foley et al. |
| 5,647,345 A | 7/1997 | Saul |
| 5,655,520 A | 8/1997 | Howe |
| 5,658,221 A | 8/1997 | Hougen |
| 5,727,546 A | 3/1998 | Clarke et al. |
| 5,791,339 A | 8/1998 | Winter |
| 5,829,429 A | 11/1998 | Hughes |
| 5,848,588 A | 12/1998 | Foley et al. |
| 5,862,802 A | 1/1999 | Bird |
| 5,890,998 A | 4/1999 | Hougen |
| 5,893,361 A | 4/1999 | Hughes |
| 5,899,832 A | 5/1999 | Hougen |
| 5,910,071 A | 6/1999 | Hougen |
| 5,925,831 A | 7/1999 | Storsved |
| 5,988,166 A | 11/1999 | Hayek |
| 6,026,807 A | 2/2000 | Puderbaugh et al. |
| 6,029,661 A | 2/2000 | Whaley et al. |
| 6,044,841 A | 4/2000 | Verdun et al. |
| 6,058,932 A | 5/2000 | Hughes |
| 6,066,101 A | 5/2000 | Johnson |
| 6,067,984 A | 5/2000 | Piper |
| 6,083,141 A | 7/2000 | Hougen |
| 6,089,105 A | 7/2000 | Ricciardelli |
| 6,102,038 A | 8/2000 | DeVries |
| 6,167,881 B1 | 1/2001 | Hughes |
| 6,176,235 B1 | 1/2001 | Benarrouch et al. |
| 6,182,657 B1 | 2/2001 | Brydon et al. |
| D440,651 S | 4/2001 | Foran |
| 6,240,917 B1 | 6/2001 | Andrade |
| 6,253,766 B1 | 7/2001 | Niles |
| 6,269,839 B1 | 8/2001 | Wickham et al. |
| 6,293,279 B1 | 9/2001 | Schmidt et al. |
| 6,340,025 B1 | 1/2002 | Van Brunt |
| 6,345,617 B1 | 2/2002 | Engelbreth et al. |
| 6,412,481 B1 | 7/2002 | Bienvenu et al. |
| 6,446,629 B1 | 9/2002 | Takaki et al. |
| 6,447,459 B1 | 9/2002 | Larom |
| 6,500,095 B1 | 12/2002 | Hougen |
| 6,557,549 B2 | 5/2003 | Schmidt et al. |
| 6,581,595 B1 | 6/2003 | Murdock et al. |
| 6,581,596 B1 | 6/2003 | Truitt |
| 6,581,598 B1 | 6/2003 | Foran et al. |
| 6,581,600 B2 | 6/2003 | Bird |
| 6,595,203 B1 | 7/2003 | Bird |
| 6,606,989 B1 | 8/2003 | Brand |
| 6,607,008 B1 | 8/2003 | Yoshimoto et al. |
| 6,615,831 B1 | 9/2003 | Truitt |
| 6,631,721 B1 | 10/2003 | Salter et al. |
| 6,659,100 B2 | 12/2003 | O'Rourke |
| 6,681,768 B2 | 1/2004 | Haaije de Boer et al. |
| 6,702,769 B1 | 3/2004 | Fowler-Hawkins |
| 6,708,690 B1 | 3/2004 | Hete et al. |
| 6,708,691 B1 | 3/2004 | Hayek |
| 6,726,598 B1 | 4/2004 | Jarvis |
| D490,519 S | 5/2004 | Pelerossi et al. |
| 6,776,159 B2 | 8/2004 | Pelerossi et al. |
| 6,848,443 B2 | 2/2005 | Schmidt et al. |
| 6,851,425 B2 | 2/2005 | Jaffre |
| 6,904,906 B2 | 6/2005 | Salter |
| 6,923,181 B2 | 8/2005 | Tuck |
| 6,929,007 B2 | 8/2005 | Emerson |
| 6,984,214 B2 | 1/2006 | Fowler-Hawkins |
| 7,059,324 B2 | 6/2006 | Pelerossi et al. |
| 7,096,866 B2 | 8/2006 | Be'eri et al. |
| 7,134,434 B2 | 11/2006 | Truitt et al. |
| 7,165,547 B2 | 1/2007 | Truitt et al. |
| 7,188,621 B2 | 3/2007 | DeVries |
| 7,191,776 B2 | 3/2007 | Niles |
| 7,191,780 B2 | 3/2007 | Faram |
| 7,214,170 B2 | 5/2007 | Summers et al. |
| 7,383,740 B2 | 6/2008 | Krasilchikov et al. |
| 7,617,821 B2 | 11/2009 | Hughes |
| 7,699,054 B2 | 4/2010 | Pelerossi et al. |
| 7,717,847 B2 | 5/2010 | Smith |
| 7,771,472 B2 | 8/2010 | Hendricksen |
| 7,779,841 B2 | 8/2010 | Dunsmore et al. |
| 7,798,148 B2 | 9/2010 | Doshi |

(56) References Cited

U.S. PATENT DOCUMENTS

| | | |
|---|---|---|
| 7,856,979 B2 | 12/2010 | Doshi |
| 7,905,228 B2 | 3/2011 | Blacker et al. |
| 7,909,033 B2 | 3/2011 | Faram |
| 8,006,922 B2 | 8/2011 | Katzer |
| 8,025,051 B2 | 9/2011 | Dagsland |
| 8,025,054 B2 | 9/2011 | Dunsmore et al. |
| 8,043,236 B2 | 10/2011 | Goldshtein et al. |
| 8,051,854 B2 | 11/2011 | Faram |
| RE43,174 E | 2/2012 | Schmidt et al. |
| 8,118,024 B2 | 2/2012 | DeVries et al. |
| 8,118,713 B2 | 2/2012 | Foley et al. |
| 8,225,785 B2 | 7/2012 | Richards et al. |
| 8,327,849 B2 | 12/2012 | Grychowski et al. |
| 8,360,061 B2 | 1/2013 | Brown |
| 8,460,223 B2 | 6/2013 | Huster et al. |
| 8,469,029 B2 | 6/2013 | Brown et al. |
| 8,485,179 B1 | 7/2013 | Meyer |
| 8,528,547 B2 | 9/2013 | Dunsmore |
| 8,539,951 B1 | 9/2013 | Meyer et al. |
| 8,985,111 B2 | 3/2015 | Grychowski et al. |
| 8,993,774 B2 | 3/2015 | Kanbara et al. |
| D731,050 S | 6/2015 | Meyer |
| 9,149,589 B2 | 10/2015 | Meyer et al. |
| 9,220,855 B2 | 12/2015 | Meyer |
| 9,358,417 B2 | 6/2016 | Meyer |
| 9,517,315 B2 | 12/2016 | Meyer |
| D776,804 S | 1/2017 | Meyer |
| D778,429 S | 2/2017 | Engelbreth et al. |
| D780,906 S | 3/2017 | Engelbreth et al. |
| 9,636,473 B2 | 5/2017 | Meyer |
| 9,737,677 B2 | 8/2017 | Grychowski et al. |
| 9,808,588 B1 | 11/2017 | Meyer et al. |
| 9,849,257 B2 | 12/2017 | Meyer et al. |
| 9,913,955 B2 | 3/2018 | Grychowski et al. |
| 9,950,128 B2 | 4/2018 | Meyer et al. |
| 9,981,106 B2 | 5/2018 | Meyer et al. |
| 10,039,691 B2 | 8/2018 | Von Hollen |
| 10,076,616 B2 | 9/2018 | Meyer et al. |
| 10,272,224 B2 | 4/2019 | Costella et al. |
| 10,363,383 B2 | 7/2019 | Alizoti et al. |
| 10,413,698 B2 | 9/2019 | Meyer et al. |
| 10,449,324 B2 | 10/2019 | Meyer et al. |
| 2003/0015195 A1 | 1/2003 | Haaije de Boer et al. |
| 2006/0032607 A1 | 2/2006 | Wisniewski |
| 2007/0017506 A1 | 1/2007 | Bell et al. |
| 2007/0089740 A1 | 4/2007 | Baumert et al. |
| 2007/0259759 A1 | 11/2007 | Sumners et al. |
| 2008/0078384 A1 | 4/2008 | Messenger et al. |
| 2008/0257348 A1 | 10/2008 | Piper |
| 2009/0241949 A1 | 10/2009 | Smutney et al. |
| 2010/0077866 A1 | 4/2010 | Graboi et al. |
| 2010/0139655 A1 | 6/2010 | Genosar |
| 2010/0207774 A1 | 8/2010 | Song |
| 2010/0307487 A1 | 12/2010 | Dunsmore et al. |
| 2011/0290240 A1* | 12/2011 | Meyer ............... A61M 16/0006 128/200.14 |
| 2012/0097164 A1 | 4/2012 | Rozario et al. |
| 2015/0374939 A1 | 12/2015 | Meyer et al. |
| 2017/0049979 A1 | 2/2017 | Meyer et al. |
| 2017/0128683 A1 | 5/2017 | Meyer et al. |
| 2017/0312461 A1 | 11/2017 | Grychowski et al. |
| 2018/0154093 A1 | 6/2018 | Meyer et al. |
| 2018/0214662 A1 | 8/2018 | Meyer et al. |
| 2018/0256839 A1 | 9/2018 | Meyer et al. |
| 2019/0240533 A1 | 8/2019 | Alizoti |

FOREIGN PATENT DOCUMENTS

| | | |
|---|---|---|
| EP | 1 464 357 A1 | 10/2004 |
| EP | 1 435 251 B1 | 6/2006 |
| EP | 1 103 287 B1 | 6/2007 |
| EP | 1 897 576 A1 | 3/2008 |
| EP | 1 908 489 A1 | 4/2008 |
| EP | 2444114 A1 | 4/2012 |
| EP | 2455137 A2 | 5/2012 |
| GB | 2 425 488 A | 11/2006 |
| WO | WO 1989/03707 A1 | 5/1989 |
| WO | WO 1996/40376 A1 | 12/1996 |
| WO | WO 1999/16490 A1 | 4/1999 |
| WO | WO 2000/27455 A1 | 5/2000 |
| WO | WO 2007/061648 A3 | 5/2007 |
| WO | WO 2007/119104 A3 | 10/2007 |
| WO | WO 2008/063966 A1 | 5/2008 |
| WO | WO 2008/122045 A1 | 10/2008 |
| WO | WO 2009/131965 | 10/2009 |
| WO | WO 2011/058470 | 5/2011 |
| WO | WO 2012/038864 A2 | 3/2012 |
| WO | WO 2016/012740 | 1/2016 |

OTHER PUBLICATIONS

Web page entitled Bronchial Hygiene, acapella Vibratory PEP Therapy System accessed from http://www.smiths-medical.com/catalog/bronchial-hygiene/acapella/acapella.html on Jul. 7, 2009.

Web page entitled Thayer Quake accessed from http://www.thayermedical.com/quake.htm on Jul. 7, 2009.

Human growth hormone, cortisol, and acid-base balance changes after hyperventilation and breath-holding; PubMed—indexed for MEDLINE; Int J Sports Med., Dec. 1986; 7(6):311-5, Djarova T.

Bosco C, Cardinale M. & Tsarpela O (1999). Influence of vibration on mechanical power and electromyogram activity in human arm flexor muscles. Eur J Appl Physiol 79, 306-311.

David Sumners; Power Breathing and Strength; http://EzineArticles.com/972576 Published: Feb. 7, 2008.

Good Vibrations blog; http://vibrotraining.blogspot.com, Earliest posting Jan. 17, 2008.

Breathtaking News; More Youbreathe; Aug. 10, 2007.

PCT International Search Report for PCT/IB2012/001089, dated Oct. 5, 2012.

PCT International Written Opinion for PCT/IB2012/001089, dated Oct. 5, 2012.

Preliminary Report on Patentability, PCT/IB2012/001089, dated Dec. 10, 2013.

PCT/IB2012001089 European Search Report dated Nov. 6, 2014.

D R Burton Healthcare LLC v. Trudell Medical International; "Petition tor Inter Partes Review of Claims 1-26 Under 35 U.S.C. §§ 311-319 and 37 C.F.R. § 42.100 et seq."; U.S. Pat. No. 9,808,588; May 4, 2018; 94 pages.

D R Burton Healthcare LLC v. Trudell Medical International; "Declaration of Dr. William W. Durgin, Ph.D., In Support of Patent Owner's Preliminary Response to Petition for Inter Partes Review"; Case No. IPR2018-01025, U.S. Pat. No. 9,808,588; Trudell Medical Exhibit 2001-00001-2001-00217; Sep. 6, 2018; 217 pages.

D R Burton Healthcare LLC v. Trudell Medical International; "Patent Owner's Preliminary Response to Petition for Inter Partes Review"; Case No. IPR2018-01025, U.S. Pat. No. 9,808,588; Sep. 7, 2018; 107 pages.

D R Burton Healthcare LLC v. Trudell Medical International; "Petitioner's Reply to Patent Owner Preliminary Response"; Case No. IPR2018-01025, U.S. Pat. No. 9,808,588 B1; Oct. 9, 2018; 16 pages.

D R Burton Healthcare LLC v. Trudell Medical International; "Decision Denying Institution of Inter Partes Review"; Case No. IPR2018-01025, U.S. Pat. No. 9,808,588 B1; Nov. 29, 2018; 32 pages.

Final Office Action for U.S. Appl. No. 14/843,662 dated Jan. 23, 2019; 22 pages.

* cited by examiner

OSCILLATING POSITIVE EXPIRATORY PRESSURE DEVICE

RELATED APPLICATIONS

This application is a continuation of U.S. application Ser. No. 15/919,790, filed on Mar. 13, 2018, pending, which is a continuation of U.S. application Ser. No. 14/946,409, filed on Nov. 19, 2015, now U.S. Pat. No. 9,950,128, which is a continuation of U.S. application Ser. No. 13/920,250, filed on Jun. 18, 2013, now U.S. Pat. No. 9,220,855, which is a continuation of Ser. No. 12/711,032, filed on Feb. 23, 2010, now U.S. Pat. No. 8,485,179, which claims the benefit of U.S. Provisional Application No. 61/154,661, filed on Feb. 23, 2009, and U.S. Provisional Application No. 61/181,200, filed on May 26, 2009, all of which are incorporated herein by reference.

TECHNICAL FIELD

The present disclosure relates to an expiratory treatment device, and in particular, to an oscillating positive expiratory pressure ("OPEP") device.

BACKGROUND

Each day, humans may produce upwards of 30 milliliters of sputum, which is a type of bronchial secretion. Normally, an effective cough is sufficient to loosen secretions and clear them from the body's airways. However, for individuals suffering from more significant bronchial obstructions, such as collapsed airways, a single cough may be insufficient to clear the obstructions.

OPEP therapy represents an effective bronchial hygiene technique for the removal of bronchial secretions in the human body and is an important aspect in the treatment and continuing care of patients with bronchial obstructions, such as those suffering from chronic obstructive lung disease. It is believed that OPEP therapy, or the oscillation of exhalation pressure at the mouth during exhalation, effectively transmits an oscillating back pressure to the lungs, thereby splitting open obstructed airways and loosening the secretions contributing to bronchial obstructions.

OPEP therapy is an attractive form of treatment because it can be easily taught to most hospitalized patients, and such patients can assume responsibility for the administration of OPEP therapy throughout their hospitalization and also once they have returned home. To that end, a number of portable OPEP devices have been developed.

BRIEF SUMMARY

In one aspect, an OPEP device comprises a housing enclosing at least one chamber, a chamber inlet configured to receive exhaled air into the at least one chamber, and a chamber outlet configured to permit exhaled air to exit the at least one chamber. A channel positioned in an exhalation flow path between the chamber inlet and the chamber outlet is movably connected to a chamber of the at least one chamber. Additionally, an air flow regulator is movable with respect to the channel between a first position, where the flow of air through the channel is restricted and a second position, where the flow of air through the channel is less restricted. The air flow regulator is configured to repeatedly move between the first position and the second position in response to a flow of exhaled air. A weight of the air flow regulator offers a resistance to the flow of exhaled air through the channel during exhalation.

In another aspect, the channel is movable about a center of rotation. The air flow regulator may comprise a center of mass offset from the center of rotation such that the channel is biased by the weight of the air flow regulator in the direction of gravity. Therefore, the channel may be configured to move with respect to the housing in response to a change in an orientation of the housing.

In another aspect, the resistance to the flow of air through the channel may be selectively adjustable independent of an orientation of the housing. For instance, the channel may comprise a truncated cone that is rotatable about an axis offset from a central axis of the truncated cone. The truncated cone may also be rotatable by a gear train extending beyond the housing.

In yet another aspect, the air flow regulator may have a spherical shape.

In another aspect, the channel is movably connected to the housing by at least one gimbal. The channel may be movable about an axis of rotation defined by a gimbal of the at least one gimbal. Furthermore, the gimbal may comprise a passage defining a portion of the exhalation flow path. Alternatively, the channel may be movably connected to the housing by a ball and socket joint.

In another aspect, the OPEP device may include a nebulizer port for receiving an aerosol medicament into the at least one chamber. The nebulizer port may also include a one-way valve configured to open during inhalation and close during exhalation. An inhalation flow path defined between the nebulizer port and the chamber inlet may bypass the channel.

In another aspect, the OPEP device may further include an indicia movable with the channel. At least a portion of the indicia is viewable from an exterior of the housing when the oscillating positive expiratory pressure device is in an orientation predetermined to be acceptable for the administration of OPEP therapy. Also, the OPEP device may include a flexible annulus disposed between the housing and the channel configured to expand in response to an increased pressure and form a seal between the housing and the channel.

In another aspect, the at least one chamber may comprise a first chamber and a second chamber, where the second chamber is movably connected to the first chamber, and the channel is movable with the second chamber.

In yet another aspect, an OPEP device includes a first chamber and a second chamber, a chamber inlet configured to received exhaled air into the first chamber, and a chamber outlet configured to permit exhaled air to exit the second chamber. A channel positioned in the second chamber in the exhalation flow path is movably connected to the first chamber. An air flow regulator positioned in the channel is configured to oscillate in response to a flow of exhaled air between a first position, where the flow of air through the channels is restricted and a second position, where the flow of air through the channel is less restricted. A weight of the air flow regulator offers a resistance to the flow of air through the channel during exhalation.

In another aspect, the second chamber may be configured to automatically move relative to the first chamber to maintain an orientation with respect to gravity. For example, the second chamber may be movably connected to the first chamber by a gimbal. As such, the channel may be movable about an axis of rotation defined by the gimbal. And, the air flow regulator may comprise a center of mass offset from the axis of rotation. Thus, the channel may be biased by the weight of the air flow regulator in a direction of gravity. The gimbal may also comprise a passage between the first chamber and the second chamber that defines a portion of the exhalation flow path.

DETAILED DESCRIPTION

Figure 1:
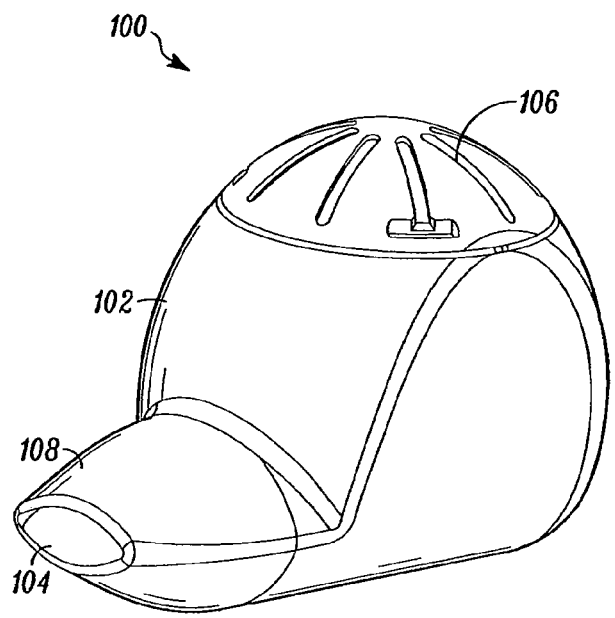
FIG. 1 is a perspective view of a first embodiment of an OPEP device.

OPEP therapy is very effective within a range of operating conditions. For example, an adult human may have an exhalation flow rate ranging from 10 to 60 liters per minute, and may maintain a static exhalation pressure in the range of 10 to 20 cm $H_2O$. Within these parameters, OPEP therapy is believed to be most effective when changes in the exhalation pressure range from 5 to 20 cm $H_2O$ oscillating at a frequency of 10 to 40 Hz. In contrast, an adolescent may have a much lower exhalation flow rate, and may maintain a lower static exhalation pressure, thereby altering the operating conditions most effective for OPEP therapy. Likewise, the ideal operating conditions for an athlete may differ from those of an adult. As described below, the preferred embodiments are configurable so that ideal operating conditions may be selected and maintained.

Referring to FIGS. 1-5, a first embodiment of an OPEP device 100 is shown. In general, the OPEP device 100 comprises a housing 102 having an interior chamber 114, a chamber inlet 104, and a chamber outlet 106. The housing 102 may also be associated with a mouthpiece 108. Although the mouthpiece 108 is shown as being fixedly attached to the housing 102, it is envisioned that the mouthpiece 108 may be removable and replaceable with a mouthpiece 108 of a different size or shape. Alternatively, other user interfaces, such as breathing tubes or gas masks (not shown) may be associated with the housing 102. Preferably, the housing 102 is openable so that the chamber 114 and the parts contained therein can be periodically accessed, cleaned, replaced, or reconfigured. The housing 102 may be constructed of any durable material, such as a polymer (e.g., Acrylonitrile butadiene styrene).

Figure 2:
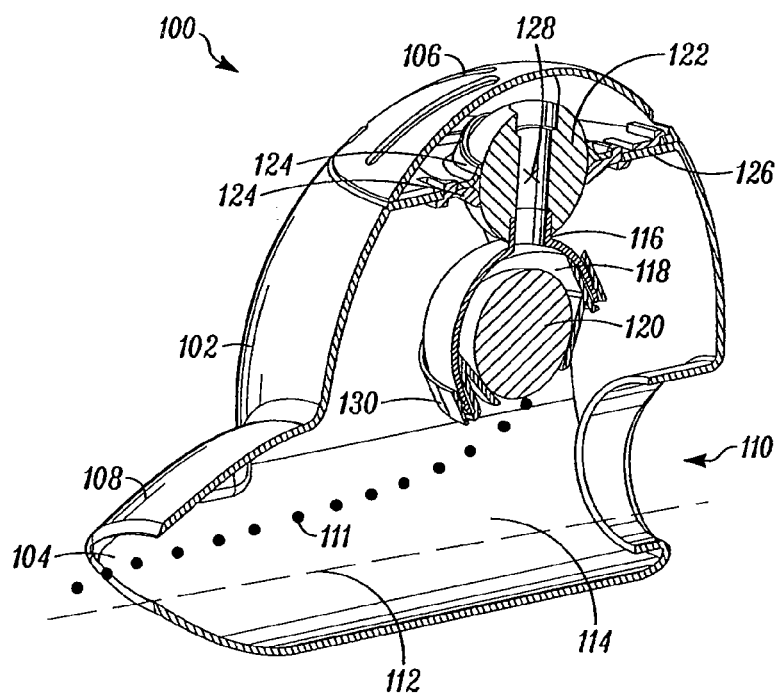
FIG. 2 is a cross-sectional perspective view of the OPEP device of FIG. 1.

In FIGS. 1-2, the housing 102 and the chamber 114 are generally spherical in shape. However, a housing of any shape could be used. Furthermore, the chamber inlet 104 and the chamber outlet 106 could be any shape or series of shapes, such as a plurality of circular passages or linear slots. More importantly, it should be appreciated that the cross-sectional area of the chamber inlet 104 is but one of the factors influencing the ideal operating conditions described above. Although these and other variables are generally described with reference to the embodiment of FIGS. 1-5, it should be understood that every embodiment described herein may be varied in a similar manner.

Referring to FIG. 2, a cross-sectional view of the OPEP device 100 is shown. The OPEP device 100 further comprises a channel assembly 116 mounted within the chamber 114. The channel assembly 116 generally includes a channel 118, an air flow regulator 120, and a rotation ball 122. The channel assembly 116 provides an exhalation flow path from the chamber 114, through the channel 118, to the chamber outlet 106. As explained in greater detail below, the channel assembly 116 is movable with respect to the housing 102. The air flow regulator 120 is also movably positioned within the channel 118, and is free to move about within the confines of at least a portion of the channel 118. The range of positions occupied by the air flow regulator 120 within the channel 118 provides varying degrees of restriction on the flow of exhaled air through the channel 118.

As shown in FIG. 2, as well as the illustrations of other embodiments described herein, the spherical shape of the air flow regulator 120 is adapted to restrict the flow of air through the channel 118. However, other sizes or shapes, such as a conical air flow regulator, could be substituted to achieve a different range of restriction. In general, the air flow regulators shown and described herein are spherical and have a diameter of five-eighths or eleven-sixteenths of an inch. Likewise, the weight of the air flow regulator 120 could be altered by changing the material of the air flow regulator 120. For instance, the air flow regulator 120 could be made from a plastic, aluminum, copper, brass, or steel. Similarly, the shape of the channel 118 could be altered to achieve a different range of restriction. For example, a portion of the channel 118 in FIG. 2 is shown as being conical, or having the shape of a truncated cone; however, one or more portions of the channel 118 could alternatively, or in combination, be spherical or cylindrical. In view of these variables, it should be appreciated that an important factor affecting the administration of OPEP therapy is the extent to which the air flow regulator 120 restricts the flow of air through the channel 118. In this way, the OPEP device 100, as well as the other embodiments described herein, is highly configurable and can be altered according to the prescribed OPEP therapy.

The OPEP device 100 shown in FIG. 2 may further include a nebulizer port 110. The nebulizer port 110 is adapted for connecting a nebulizer (see FIG. 5) to the OPEP device 100 for the simultaneous administration of OPEP and aerosol therapies, as explained in more detail below. The nebulizer port 110 may also include a one-way valve (not shown) configured to open on inhalation and close on exhalation. In this configuration, an inhalation flow path is formed between the nebulizer port 110 and the chamber inlet 104 via the chamber 114, as indicated by a dashed line 112. If the OPEP device 100 is connected to a nebulizer, an aerosol medicament may be drawn from the nebulizer into the respiratory system of the user upon inhalation. If the OPEP device 100 is not connected to a nebulizer, the user may inhale through the nebulizer port 110 the air surrounding the OPEP device 100, or air from a stand-alone air supply connected to the nebulizer port 110. However, in both cases, exhaled air is forced to traverse the channel 118 and exit the OPEP device 100 through the chamber outlet 106. Alternatively, the OPEP device 100 may include a separate inhalation valve (not shown) or omit the nebulizer port 110 altogether, in which case the user would have to inhale through a source external to the OPEP device 100, such as through his or her nose. It should be appreciated that each embodiment described herein may be adapted in a similar manner to provide the simultaneous administration of OPEP and aerosol therapies.

Figure 3:
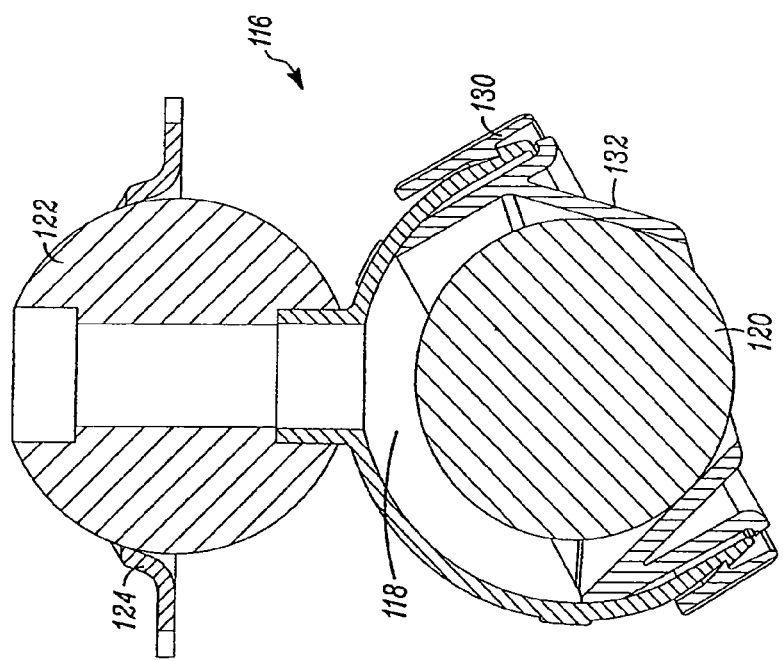
FIG. 3 is a cross-sectional side view of a channel assembly of the OPEP device of FIG. 1, showing an air flow regulator in a first position in the channel.
Figure 5:
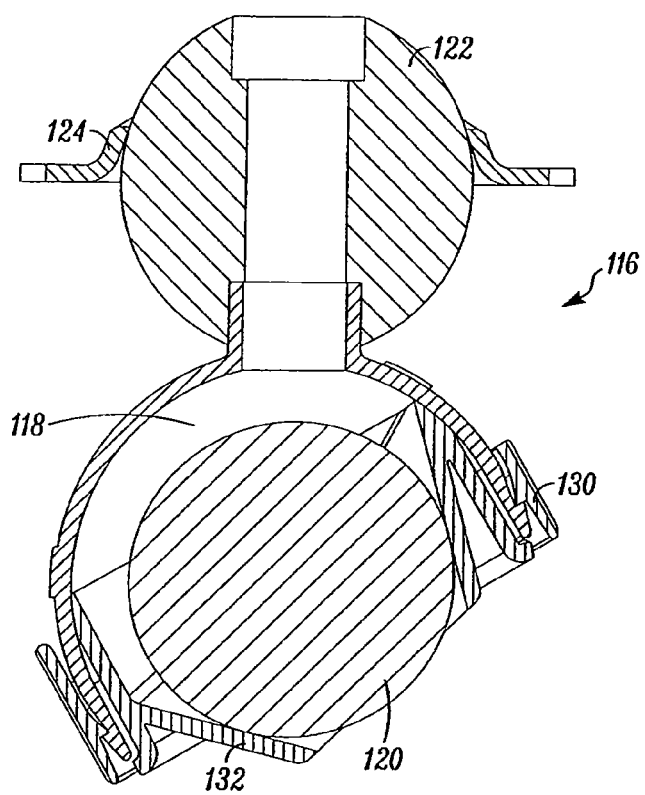
FIG. 5 is a cross-sectional side view of the channel assembly of the OPEP device of FIG. 1, showing one possible configuration for a portion of the channel.

In operation, the OPEP device 100 administers OPEP therapy to a user while he or she exhales into the chamber inlet 104. When the OPEP device 100 is positioned in an upright orientation, as shown in FIG. 1, the air flow regulator 120 moves under the force of gravity into a first position, or a resting position, as shown in FIGS. 2-3. With the air flow regulator 120 in the first position, the flow of air through the channel 118 is restricted, as indicated in FIG. 2 by a dotted line 111 traversing a portion of the exhalation flow path. Depending on the shape and size of the air flow regulator 120 and/or the channel 118, the air flow regulator 120 may restrict some or all of the exhaled air flowing through the channel 118. As the user continues to exhale, the pressure within the chamber 114 increases. As the pressure increases, the force acting on the portion of the air flow regulator 120 restricting the flow of exhaled air through the channel 118 also increases. The force acting on the air flow regulator 120 continues to increase during exhalation until the force of gravity acting on the air flow regulator 120 is overcome, and the air flow regulator 120 moves from the first position to a second position in the channel 118, as shown only by way of example in FIG. 4.

In the second position, the air flow regulator 120 is lifted away from the resting position near the bottom of the channel 118. Depending on the shape and size of the air flow regulator 120 and/or the channel 118, the air flow regulator 120 may roll, slide, or jump to the second position. With the air flow regulator 120 in the second position, the flow of air through the channel 118 is less restricted than the flow of air through the channel 118 when the air flow regulator 120 is in the first position. As indicated by the dotted line 111 traversing a portion of the exhalation flow path, more air is permitted to traverse the channel 118 and exit the chamber outlet 106. In this way, the weight of the air flow regulator 120 offers a resistance to the flow of exhaled air through the channel 118 during exhalation.

After the airflow regulator 120 moves to the second position, and the flow of air through the channel 118 increases, the pressure in the chamber 114 begins to drop. As the pressure decreases, the force acting on the portion of the air flow regulator 120 restricting the flow of air through the channel 118 also decreases. When this force drops below the force of gravity acting on the air flow regulator 120, the air flow regulator 120 returns to the first position, thereby increasing the restriction on the flow of air through the channel 118, and causing the pressure in the chamber 114 to rise again. As a user continues to exhale, this process repeats itself, effectively generating an oscillating pressure in the chamber 114. This oscillating pressure is in turn transmitted back through the chamber inlet 104 and into the respiratory system of the user, providing him or her with OPEP therapy.

One advantage of the OPEP device 100 is its ability to reduce the effect of the orientation of the OPEP device 100 on the effective administration of OPEP therapy. Returning to FIG. 3, a cross-sectional side view of the channel assembly 116 is shown. As previously explained, the weight of the air flow regulator 120 offers a resistance to the flow of air through the channel 118. While the air flow regulator 120 is in the first position, the force of gravity acting on the air flow regulator 120 is balanced by the force derived from the exhalation pressure in the chamber 114 and the normal force from the channel 118 acting on the air flow regulator 120. Accordingly, if the orientation of the channel 118 were to change, the magnitude and direction of the normal force from the channel 118 would change, as would the direction of the force acting on the air flow regulator 120 derived from the exhalation pressure in the chamber 114. The direction and magnitude of gravitational forces acting on the air flow regulator 120, however, would remain unchanged. Put another way, a change in the orientation of the OPEP device 100 may increase or decrease the incline of the channel 118 the air flow regulator 120 must traverse to arrive at the second position. Thus, the orientation of the channel 118, along with the position of the air flow regulator 120 within the channel 118, could prevent the air flow regulator 120 from sufficiently restricting the flow of air through the channel 118, such that the administration of OPEP therapy would not be possible.

To that end, as shown in FIG. 2, the channel assembly 116 is movably connected to the housing by a ball and socket joint. As such, the channel assembly 116 is rotatable in any direction with respect to the housing 102 about a center of rotation 128 located at the center of a rotation ball 122. More specifically, the channel assembly 116 is supported within the chamber 114 by a pair of socket walls 124 surrounding a portion of the rotation ball 122. The socket walls 124 are conically shaped and create a seal around the rotation ball 122. To aid in the creation of a seal around the rotation ball 122, yet maintain mobility of the channel assembly 116, the socket walls 124 and the rotation ball 122 may be made of suitable low friction materials (e.g., acetyl, nylon, etc.). Alternatively, a lubricant could be applied to the rotation ball 122 and the socket walls 124. The socket walls 124 are in turn connected to a support plate 126 extending from the housing 102. Although the socket walls 124, the support plate 126, and the housing 102 are shown as being connected via snap-fits, any other suitable means of removable connection could be used.

Thus, as a user changes the orientation of the OPEP device 100, the channel assembly 116 is free to rotate in any direction about the center of rotation 128 and within the confines of the chamber 114. For example, and depending on the shape and size of the housing 102, as well as the location of the ball and socket joint contained therein, the channel assembly 116 may be able to rotate plus or minus ninety degrees in a given direction before hitting the housing 102, the support plate 126, or a socket wall 124. However, the force of gravity acting on the channel assembly 116, and in particular the air flow regulator 120, biases the channel assembly 116 in the direction of gravity. Accordingly, as the user changes the orientation of the OPEP device 100, the channel assembly 116 moves with respect to the housing 102 so that it maintains alignment with the direction of gravity, and in an orientation that permits the administration of OPEP therapy. In this way, the channel 118 maintains alignment with the direction of gravity so long as the user does not move the housing to an orientation beyond the permissible range of movement of the channel assembly 118 (i.e., plus or minus a specific number of degrees in a given direction).

Figure 4:
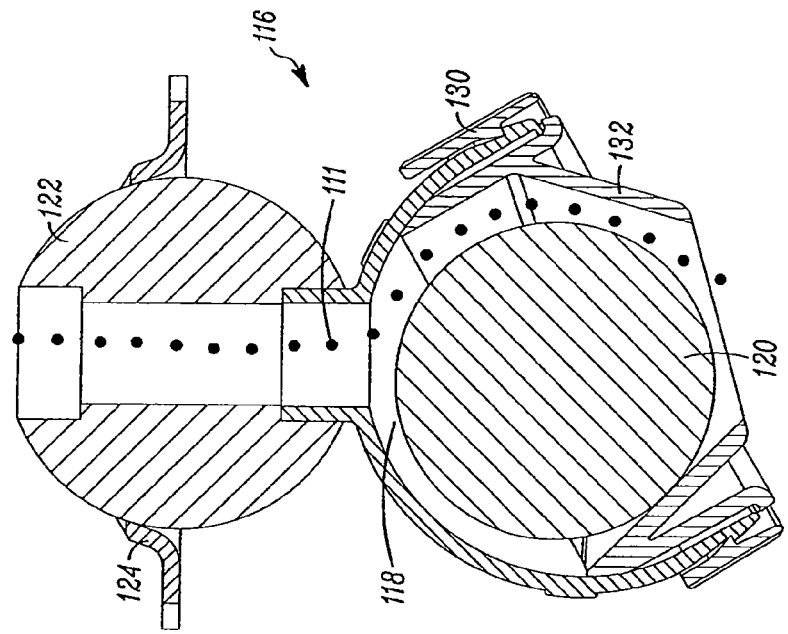
FIG. 4 is a cross-sectional side view of the channel assembly of the OPEP device of FIG. 1, showing the air flow regulator in a second position in the channel.

The OPEP device 100 is further configurable in that the magnitude and direction of the normal force from the channel 118 acting on the air flow regulator 120 is adjustable. As shown in FIGS. 2-5, a user may open the housing 102 to access the chamber 114 and change the configuration of a portion of the channel 118 via a dial 130. The dial 130 is disposed about an end of the channel assembly 116 and is connected to a truncated cone 132. The axes of the dial 130 and the truncated cone 132 are misaligned such that rotation of the dial 132 causes an asymmetrical rotation of the truncated cone 132. Put another way, a user may change the incline of the channel 118 the air flow regulator 120 must traverse to arrive at the second position by rotating the dial 132. In this way, the user is able to adjust the magnitude and direction of the normal force acting on the air flow regulator 120 such as, for example, from a lower setting shown in FIGS. 3-4, to a higher setting shown in FIG. 5. In turn, the exhalation pressure required to move the air flow regulator from the first position to the second position for the configuration in FIGS. 3-4 is greater than the pressure required in the configuration of FIG. 5. Likewise, the frequency at which the air flow regulator 120 moves between the first position and the second position is greater for the configuration shown in FIGS. 3-4 than it is for the configuration shown in FIG. 5. By selecting various configurations of the truncated cone 132, the user is able to further configure the OPEP device 100 according to his or her prescribed OPEP therapy.

Figure 6:
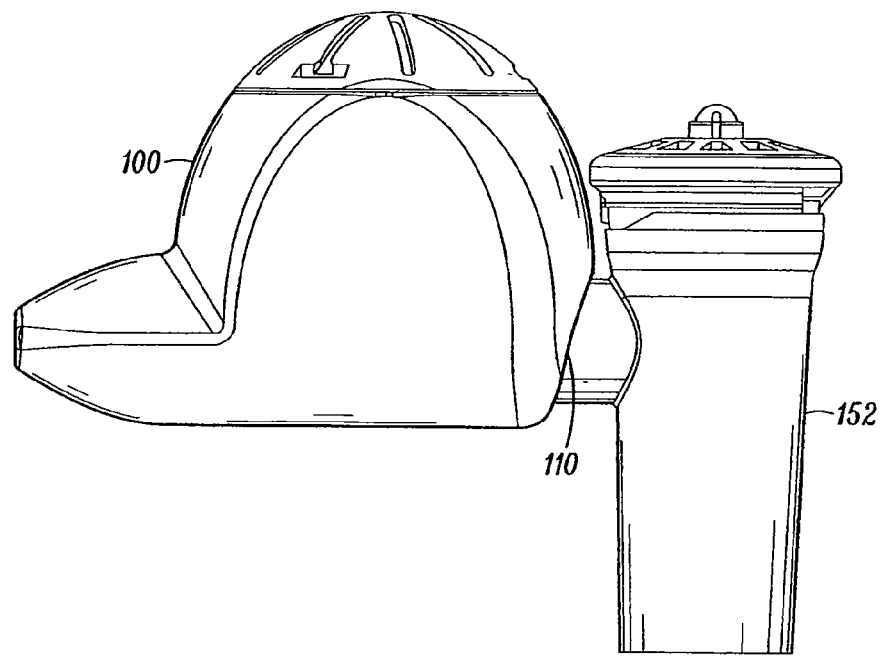
FIG. 6 is a side view of the OPEP device of FIG. 1 connected to a nebulizer for the combined administration of OPEP and aerosol therapies.

Referring to FIG. 6, a side view is shown of the OPEP device 100 connected to a nebulizer 152 via the nebulizer port 110 for the combined administration of OPEP and aerosol therapies. Any of a number of commercially available nebulizers may be used with the OPEP device 100. One suitable nebulizer is the AeroEclipse® II breath actuated nebulizer available from Trudell Medical International of London, Canada. Descriptions of suitable nebulizers may be found in U.S. Pat. No. 5,823,179, the entirety of which is hereby incorporated by reference herein.

Figure 7:
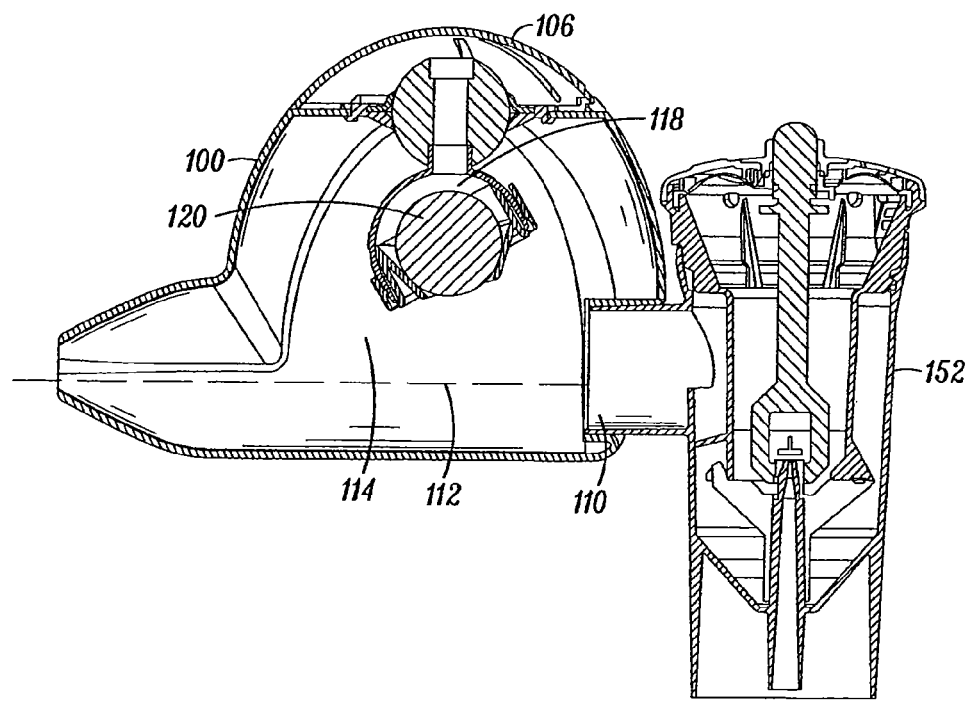
FIG. 7 is a cross-sectional side view of the OPEP device of FIG. 1 connected to a nebulizer for the combined administration of OPEP and aerosol therapies.

Turning to FIG. 7, a cross-sectional side view is shown of the OPEP device 100 and the nebulizer 152. The nebulizer 152 may be removably connected to the OPEP device 100 by any suitable means. As previously explained, in this configuration, a user receives OPEP therapy upon exhalation, and aerosol therapy upon inhalation. As a user exhales, the one way valve (not shown) associated with the nebulizer port 110 closes, forcing exhaled air to exit the chamber 114 through the channel 118 and the chamber outlet 106. In contrast, as a user inhales, the air flow regulator 120 restricts the flow of air through the channel 118, and the one way valve opens, permitting an aerosol medicament to be drawn from the nebulizer 152 through the chamber 114 and into the user.

One advantage of the embodiment of FIGS. 6-7 is that the inhalation flow path from the nebulizer port 110 to the chamber inlet 102 bypasses the channel 118, as indicated by the dashed line 112. As such, when the OPEP device 100 is connected to the nebulizer 152, aerosol medicament does not get stuck in the channel 118. In this manner, loss of medicament and contamination of the channel 118 is may be reduced. Although the configuration in FIGS. 6-7 is shown in relation to the OPEP device 100, it should be appreciated that any of the embodiments disclosed herein could be similarly adapted for the combined administration of OPEP and aerosol therapies.

Figure 8:
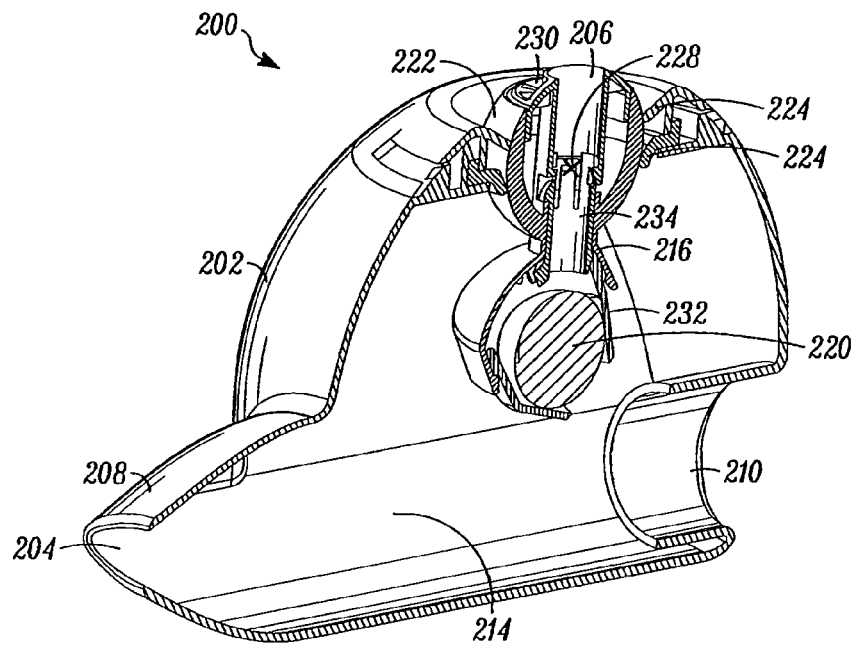
FIG. 8 is a cross-sectional perspective view of a second embodiment of an OPEP device.

Turning to FIG. 8, a cross-sectional perspective view of a second embodiment of an OPEP device 200 is shown. In general, the OPEP device 200 comprises the same components as the OPEP device 100. More specifically, the OPEP device 200 comprises a housing 202, a chamber inlet 204, a chamber outlet 206, a mouthpiece 208, a nebulizer port 210 having a one way valve (not shown), a chamber 214, and a channel assembly 216. As with the OPEP device 100, the channel assembly 216 in the OPEP device 200 is connected to the housing 202 by a ball and socket joint, comprising a pair of socket walls 224 and a rotation ball 222.

Figure 9:
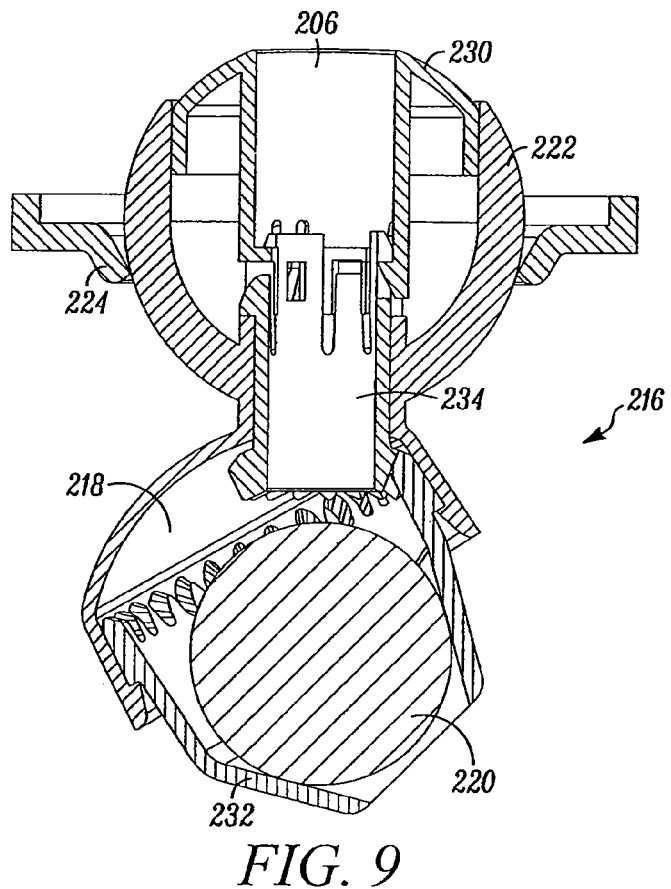
FIG. 9 is a cross-sectional side view of a channel assembly of the OPEP device of FIG. 8.
Figure 10:
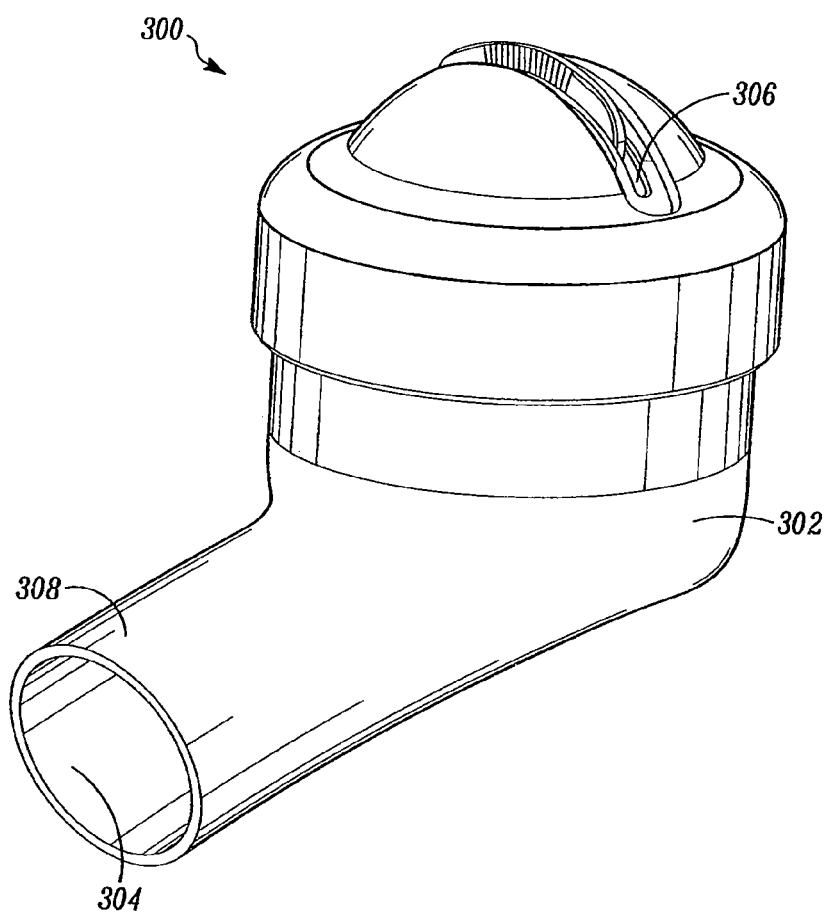
FIG. 10 is a perspective view of a third embodiment of an OPEP device.

Referring to FIGS. 8-9, the OPEP device 200 differs from the OPEP device 100 in that a user does not have to open the housing 202 to adjust the magnitude and direction of the normal force from the channel 218 acting on the air flow regulator 220. Rather, the OPEP device 200 comprises a gear train 234 that is connected to a truncated cone 232 and that extends through the rotation ball 222 to a dial 230 accessible by the user. As shown in FIG. 9, the gear train 234 is adapted to rotate relative to the rotation ball 222 and defines a portion of the exhalation flow path leading from the chamber 214 to the chamber outlet 206. Thus, a user can adjust the direction and magnitude of the normal force acting on the air flow regulator 220 by rotating the dial 230, which in turn drives the gear train and changes the configuration of the truncated cone 232. The OPEP device 200 is therefore configurable for a prescribed OPEP therapy in the same manner as the OPEP device 100. In all other aspects, the OPEP device 200 administers OPEP therapy in the same way as described above in relation to the OPEP device 100.

Turning to FIGS. 10-21, a third embodiment of an OPEP device 300 is shown. The OPEP device 300 comprises a housing 302, a chamber inlet 304, a chamber outlet 306, and a mouthpiece 308. Although the OPEP device 300 is not shown as having a nebulizer port for connection to a nebulizer, a nebulizer port could be included in the same manner as described above in relation to the OPEP device 100.

Figure 11:
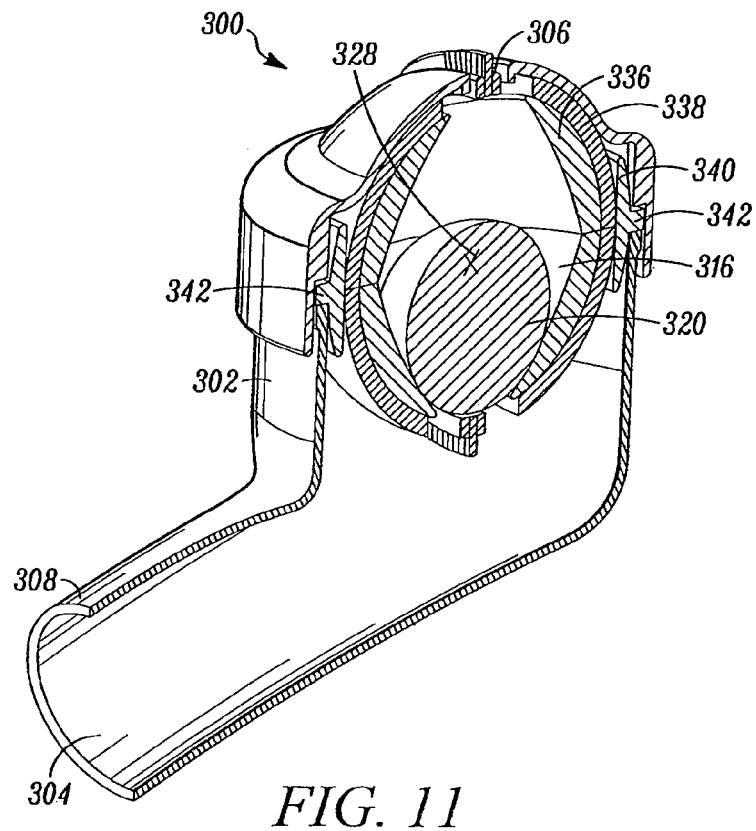
FIG. 11 is a cross-sectional perspective view of the OPEP device of FIG. 10.
Figure 12:
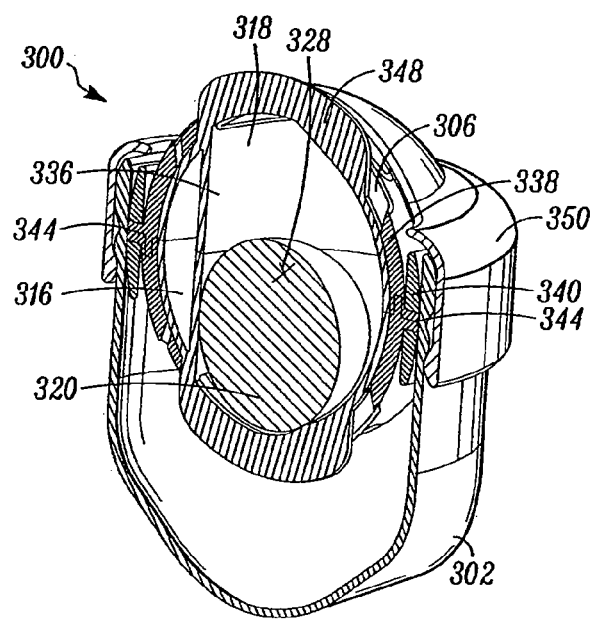
FIG. 12 is a different cross-sectional perspective view of the OPEP device of FIG. 10.

Referring to FIG. 11, a cross-sectional view of the OPEP device 300 is shown. The OPEP device 300 includes a channel assembly 316 comprising an air flow regulator 320, a cup 336, an inner sphere 338, and an outer ring 340. A channel 318 is defined within the cup 336 and the inner sphere 338. As shown, the channel assembly 316 is movably connected to the housing 302 by a first gimbal 342 such that the channel assembly 316 is rotatable about an axis defined between the first gimbal 342. Likewise, referring to FIG. 12, the inner sphere 338 is connected to the outer ring 340 by a second gimbal 344, offset ninety degrees from the first gimbal 342, such that the inner sphere 338 is rotatable about an axis defined between the second gimbal 344. As such, the cup 336, the inner sphere 338, and the channel 318 are rotatable in any direction relative to the housing 302 about a center of rotation 328. In this embodiment, the center of rotation 328 is located at the intersection of the axes defined by the first gimbal 342 and the second gimbal 344. As in the OPEP device 100 and the OPEP device 200, the weight of the air flow regulator 320 biases the channel assembly 318 in the direction of gravity. Thus, as a user changes an orientation of the housing 302, the channel assembly 316 moves relative to the housing 302 so that the channel 318 maintains alignment with the direction of gravity, and in an orientation that permits the administration of OPEP therapy.

Figure 13:
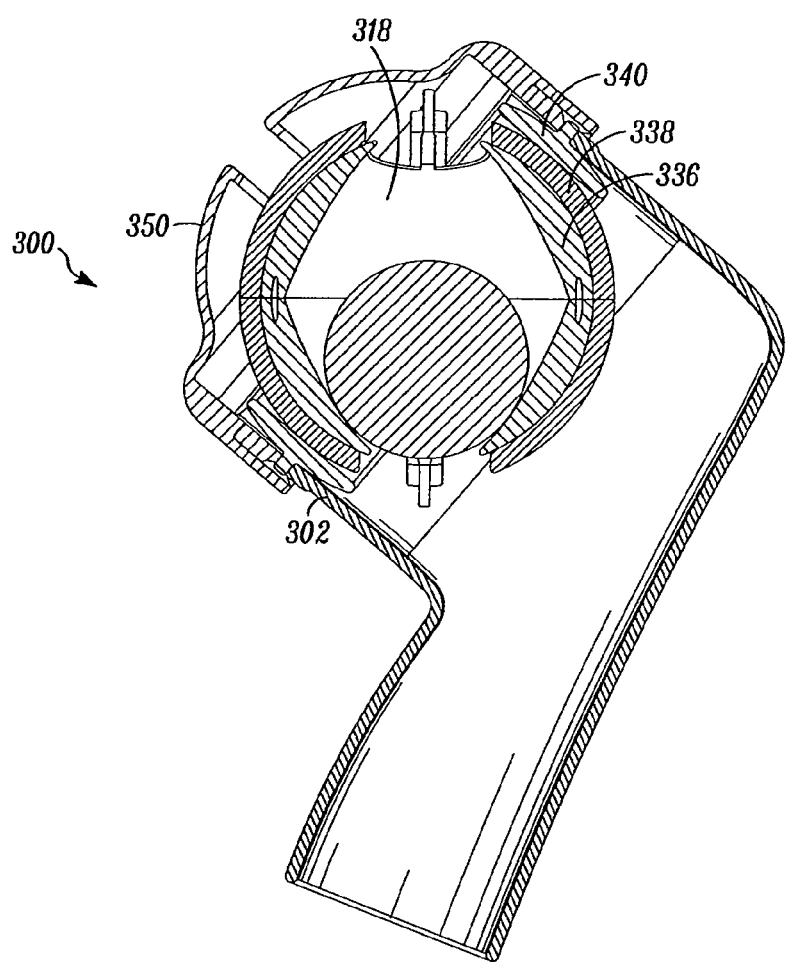
FIG. 13 is a cross-sectional side view of the OPEP device of FIG. 10, showing a channel maintaining alignment with a direction of gravity as an orientation of the OPEP device is rotated about a first axis.
Figure 14:
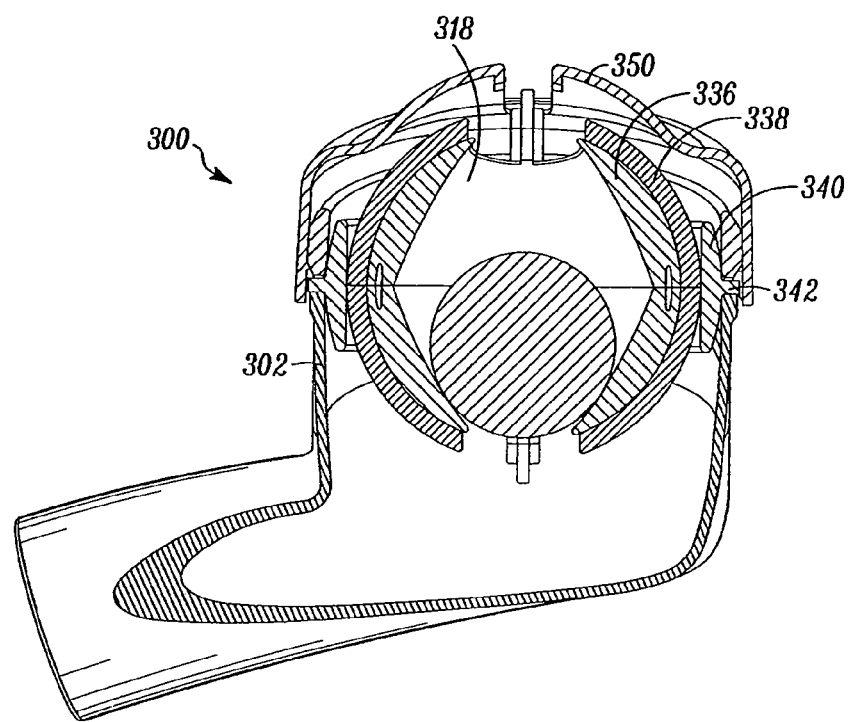
FIG. 14 is a cross-sectional side view of the OPEP device of FIG. 10, showing the channel maintaining alignment with the direction of gravity as the orientation of the OPEP device is rotated about a second axis.
Figure 15:
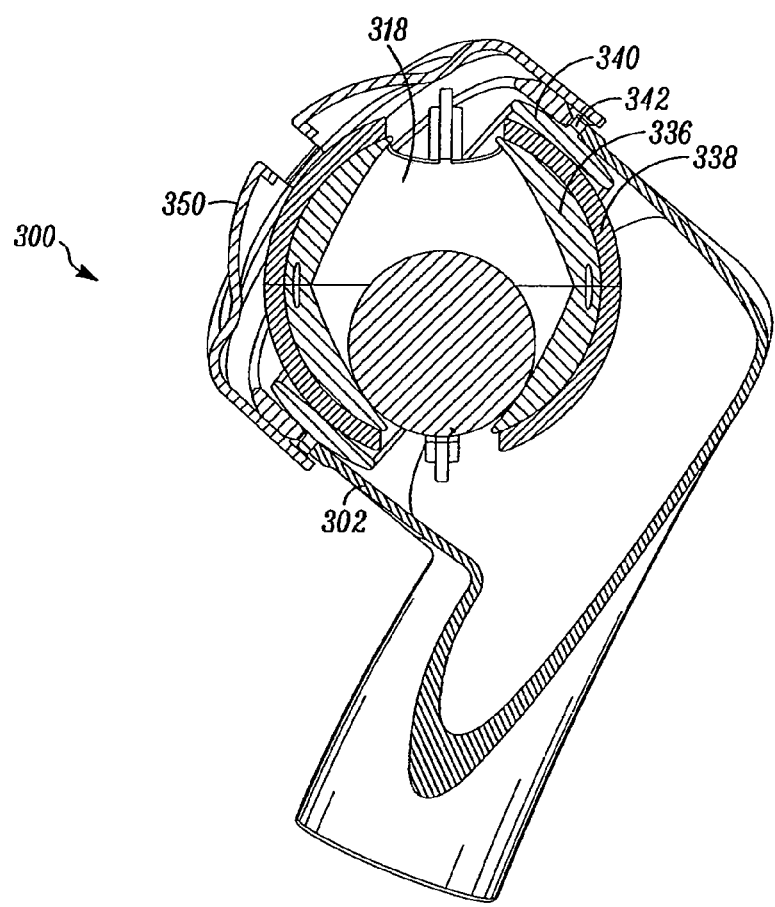
FIG. 15 is a cross-sectional side view of the OPEP device of FIG. 10, showing the channel maintaining alignment with the direction of gravity as the orientation of the OPEP device is rotated about both the first axis and the second axis.

FIGS. 13-15 illustrate movement of the channel assembly 318 relative to the housing 302 in response to a change in the orientation of the OPEP device 300. FIG. 13 is a cross sectional-side view of the OPEP device 300, showing alignment of the channel assembly 318 with the direction of gravity when the orientation of the OPEP device 300 is rotated about the axis defined between the second gimbal 344 (see FIG. 12). In this orientation, the cup 336 and the inner sphere 338 are rotated relative to the housing 302 about the second gimbal 344, while the outer ring 340 remains substantially unmoved. Similarly, FIG. 14 shows a cross-sectional side view of the OPEP device 300 in an orientation where the OPEP device 300 is rotated about the axis defined between the first gimbal 342. In this orientation, the cup 336, the inner sphere 338, and the outer ring 340 are all rotated relative to the housing 302 about the axis defined between the first gimbal 342. Finally, FIG. 15 shows a cross-sectional side view of the OPEP device 300 in an orientation where the OPEP device 300 is rotated about both the axis defined between the second gimbal 344 and the first gimbal 342. In this orientation, the cup 336 and the inner sphere 338 are rotated relative to the housing 302 about the axis defined between the second gimbal 344, while the outer ring 340 is rotated relative to the housing 302 about the axis defined between the first gimbal 342. In each instance, the channel assembly 318 moves relative to the housing 302 in a direction opposite the change in orientation of the OPEP device 300, thereby maintaining alignment of the channel assembly 318 with the direction of gravity and permitting the administration of OPEP therapy.

Figure 16:
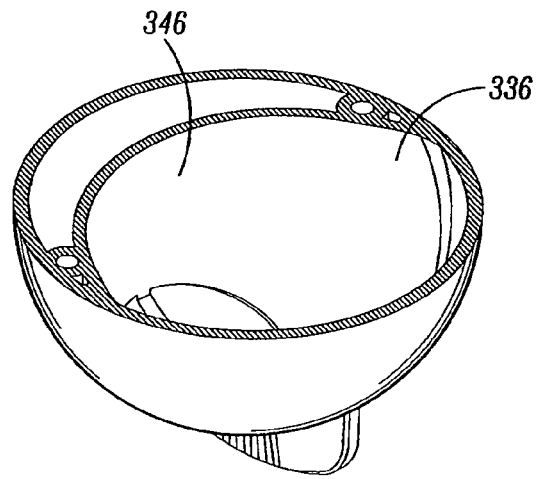
FIG. 16 is a perspective view of a cup of the OPEP device of FIG. 10.

During the administration of OPEP therapy, the cup 336 and the inner sphere 338 are frictionally engaged such that they move in unison. However, the cup 336 is also selectively rotatable relative to the inner sphere 338 to provide an adjustable normal force form the channel 318 on the air flow regulator 320. Referring to FIG. 16, a perspective view of a lower portion of the cup 336 is shown. The cup 336 of the OPEP device 300 is openable so that the air flow regulator (not shown) may be accessed for cleaning and replacement. As shown, the cup 336 is configured to have an asymmetrical surface 346. However, the cup 336 could have any number of alternative configurations. The asymmetrical surface 346, like the truncated cone in the OPEP device 100 and the OPEP device 200, is configured to supply a variable normal force on the air flow regulator 320, dependent on the orientation of the cup 336.

Figure 17:
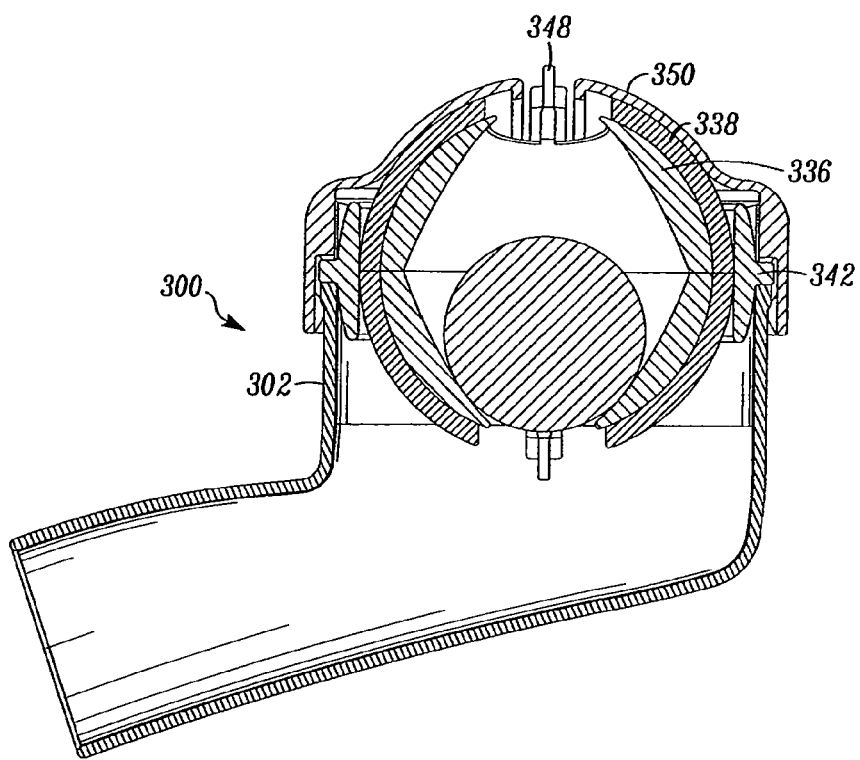
FIG. 17 is a cross-sectional side view of the OPEP device of FIG. 10, showing an upper portion of a housing in a locked position.

Returning to FIG. 12, a tab 348 connected to the cup 336 extends through the outer sphere 338 and the chamber outlet 306 to provide the user with a means of rotating the cup 336 relative to the inner sphere 338. Significantly, the tab 348 is aligned with the axis extending between the second gimbal 344 so as to prevent the inner sphere 338 from rotating relative to the outer ring 340 while the cup 336 is being rotated. Even then, rotation of the cup 336 would cause the inner sphere 338 and the outer ring 340 to rotate about the axis formed between the first gimbal 342. Accordingly, an upper portion 350 of the housing 302 is configured to selectively move between an unlocked position, as shown in FIGS. 13-15, and a locked position, as shown in FIG. 17. In the unlocked position, the upper portion 350 is disengaged with the inner sphere 338 such that the inner sphere 338 may rotate relative to the housing 302. In the locked position, the upper portion 350 engages the inner sphere 338 and prevents its rotation. In this way, a user may press down on the upper portion 350 to move the upper portion 350 from the unlocked position to the locked position, and then use the tab 348 to rotate the cup 336 relative to the inner sphere 338. A means for biasing (not shown) the upper portion 350 to the unlocked position may be also be provided. Alternatively, the cup 336 and the inner sphere 338 could be mechanically engaged so that they move in unison, but still be movable relative to one another, such as by means of a detent.

Figure 18:
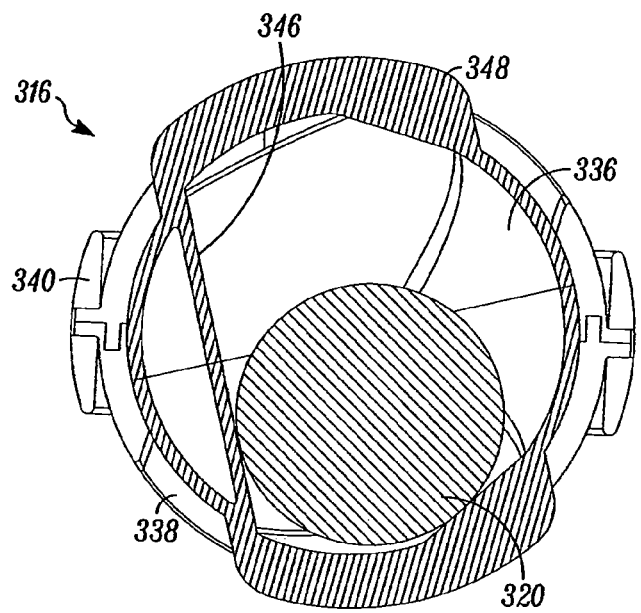
FIG. 18 is a cross-sectional front view of a channel assembly of the OPEP device of FIG. 10, showing the channel in one possible orientation.
Figure 19:
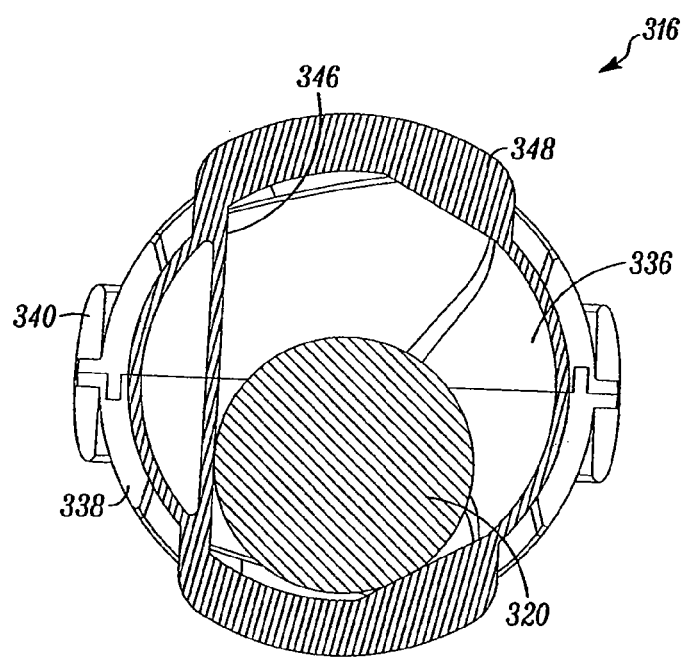
FIG. 19 is a cross-sectional front view of the channel assembly of the OPEP device of FIG. 10, showing the channel in another possible orientation.
Figure 20:
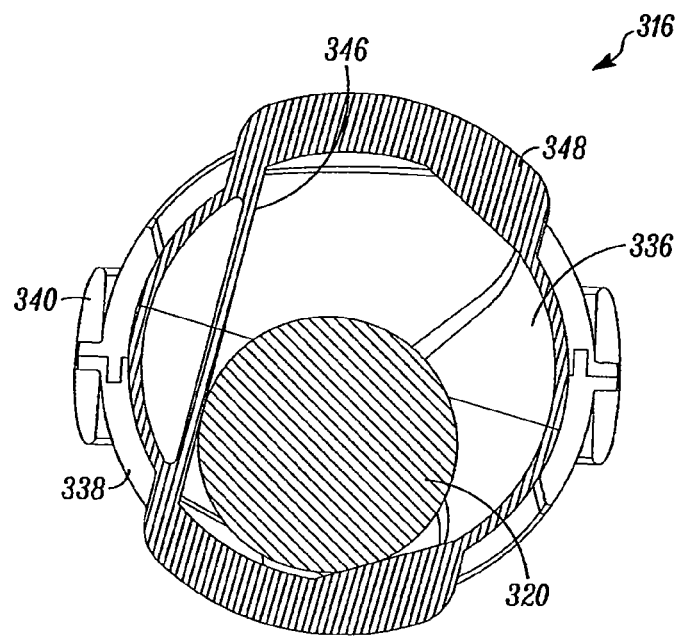
FIG. 20 is a cross-sectional front view of the channel assembly of the OPEP device of FIG. 10, showing the channel in yet another possible orientation.

Referring to FIGS. 18-20, cross-sectional side views are shown of the cup 336 in different orientations within the channel assembly 316 of the OPEP device 300. In FIG. 18, the cup 336 is shown in an orientation such that the magnitude and direction of the normal force acting on the air flow regulator 320 require a larger exhalation pressure in the chamber to move the air flow regulator 320 from the first position to the second position. In other words, the air flow regulator 320 must traverse a steeper incline in the channel 318 to arrive at the second position. Similarly, the orientation of the cup 336 shown in FIG. 19 requires an intermediate exhalation pressure, and the orientation of the cup 336 shown in FIG. 20 requires a smaller exhalation pressure. In this way, a user is able to selectively adjust the operating parameters of the OPEP device 300 by moving the upper portion 350 into the locked position and using the tab 348 to change the orientation of the cup 336.

Figure 21:
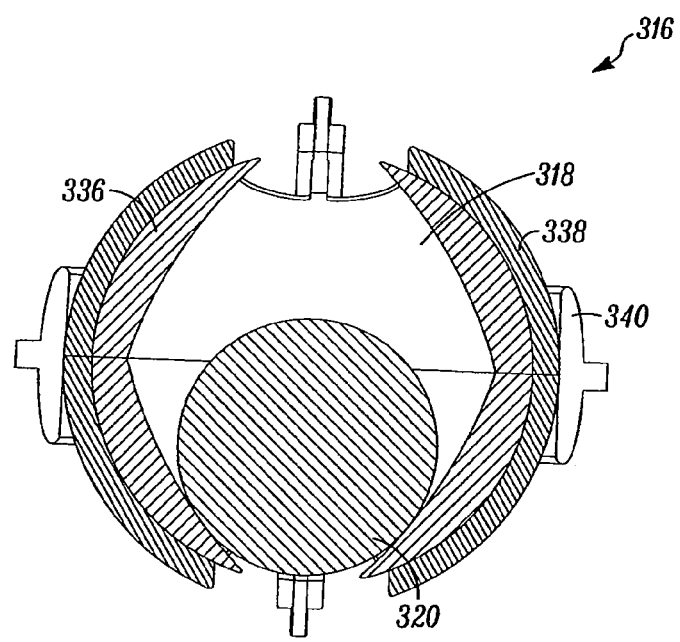
FIG. 21 is a cross-sectional side view of the channel assembly of the OPEP device of FIG. 10, showing a seal between the housing and an outer ring, the outer ring and an inner sphere, and the inner sphere and the cup.
Figure 22:
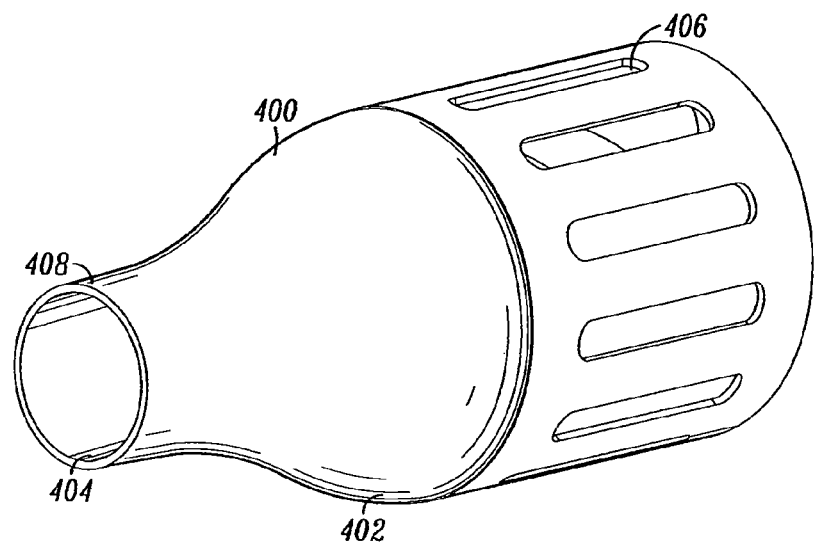
FIG. 22 is a perspective view of a fourth embodiment of an OPEP device.

Turning to FIG. 21, a cross-sectional side view of the channel assembly 316 of the OPEP device 300 is shown. In order for the OPEP device 300 to effectively administer OPEP therapy, a seal must be formed between the housing 302 and the outer ring 340, the outer ring 340 and the inner sphere 338, and the inner sphere 338 and the cup 336. For the interfaces between the housing 302 and the outer ring 340, as well as between the outer ring 340 and the inner sphere 338 (i.e., components that are free to move under the weight of the air flow regulator 320), a seals is created between appropriately sized cylindrical and spherical surfaces. For the interface between the inner sphere 338 and the cup 336 (i.e., parts that are not free to move under the weight of the air flow regulator 320), a seal is created between appropriately sized spherical surfaces, which also provides friction sufficient to permit the inner sphere 338 and the cup 336 to move in unison. As such, exhaled air is forced through the channel 318 during the administration of OPEP therapy. In all other aspects, the OPEP device 300 administers OPEP therapy in the same way as described above in relation to the OPEP device 100.

It should be appreciated that the seal formed between the housing 302 and the outer ring 340 is maintainable for a specific range of movement, the limits of which are defined by the shape and size of the housing 302 and the outer ring 340. For instance, a significant change in the orientation of the OPEP device 300 may cause the outer ring 340 to rotate relative to the housing 302 about the first gimbal 342 to a position where the cylindrical surface of the housing 302 and the spherical surface of the outer ring 340 are no longer in a sealing engagement.

Figure 23:
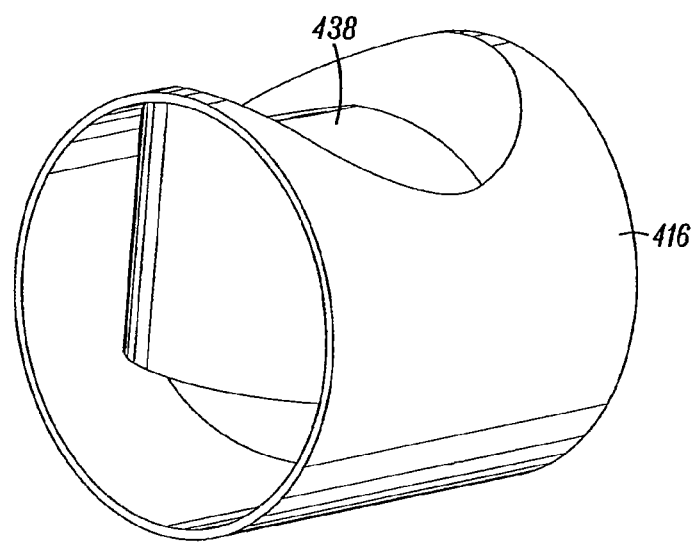
FIG. 23 is a perspective view of a channel assembly of the OPEP device of FIG. 22.

Referring to FIGS. 22-25, a fourth embodiment of an OPEP device 400 is shown. In general, the OPEP device 400 comprises a cylindrical housing 402, a chamber inlet 404, a chamber outlet 406, and a mouthpiece 408. As shown in FIG. 23, the OPEP device 400 further comprises a channel assembly 416 that includes an inner sphere 438. The channel assembly 416 is cylindrically shaped and sized so that the housing 402 circumscribes the channel assembly 416 in a manner allowing the channel assembly 416 to rotate with respect to the housing 402. In this way, the channel assembly 416 and the inner sphere 438 are rotatable with respect to the housing 402 about an axis of rotation defined by a central axis of the housing 402 and the channel assembly 416. As previously explained, suitable low friction materials or a lubricant may be to aid the relative movement of the housing 402 and the channel assembly 416.

Figure 24:
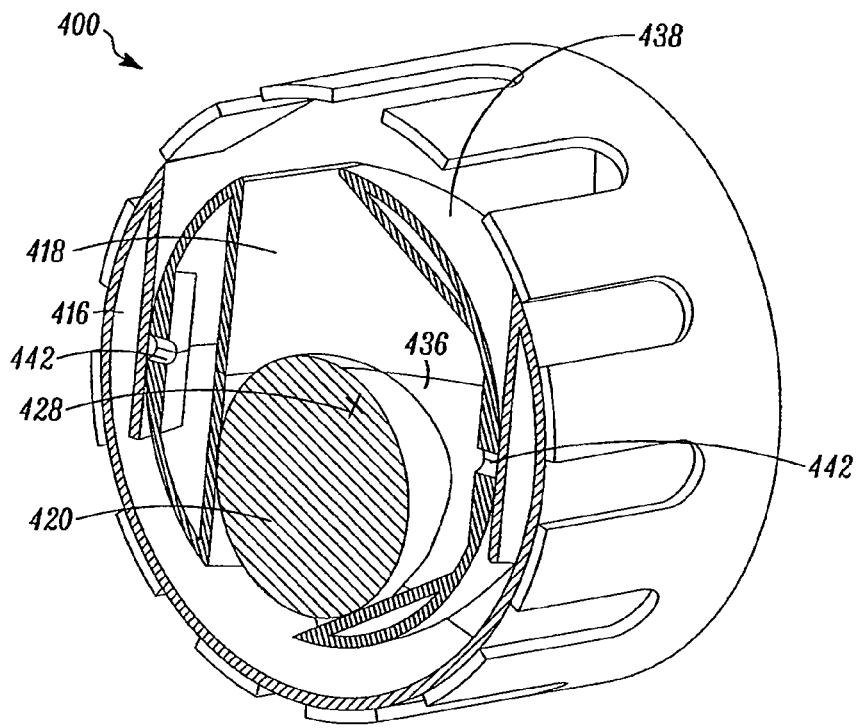
FIG. 24 is a cross-sectional perspective view of the OPEP device of FIG. 22.

Turning to FIG. 24, a cross-sectional perspective view of the OPEP device 400 is shown. The channel assembly 416 of the OPEP device 400 further comprises a channel 418, an air flow regulator 420, a cup 436, and an inner sphere 438. The inner sphere 438 is connected to the channel assembly 416 by a gimbal 442 such that the inner sphere 438 is rotatable relative to the channel assembly 416 about an axis defined between the gimbal 442. As such, the inner sphere 438 and the channel 418 are rotatable in any direction with respect to the housing 402 about a center of rotation 428. In this embodiment, the center of rotation 428 is located at the intersection of the central axis of the housing 402 and the axis defined between the gimbal 442. Moreover, like the previously described OPEP devices, the weight of the air flow regulator 420 biases the channel 418 in the direction of gravity. Thus, as a user changes an orientation of the housing 402, the channel 418 moves relative to the housing 402 under the weight of the air flow regulator 420 such that the channel 418 maintains alignment with the direction of gravity, and in an orientation that permits the administration of OPEP therapy.

Figure 25:
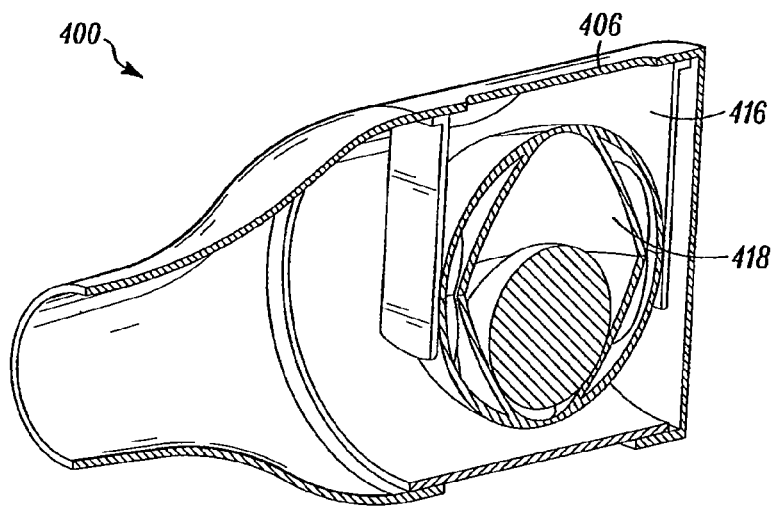
FIG. 25 is a different cross-sectional perspective view of the OPEP device of FIG. 22.

Turning to FIG. 25, a different cross-sectional view of the OPEP device 400 is shown. The OPEP device 400 and the channel assembly 416 are configured to force exhaled air to pass through the channel 418 and out the chamber outlet 406 during the administration of OPEP therapy. However, because the OPEP device 400 shown in FIG. 18 does not include a nebulizer port, a user would have to inhale through a source external to the OPEP device 400, such as through his or her nose. Alternatively, the OPEP device 400 could include a separate inhalation valve to facilitate inhalation through the OPEP device 400. In all other aspects, the OPEP device 400 administers OPEP therapy in the same way as described above in relation to the OPEP device 100.

Figure 26:
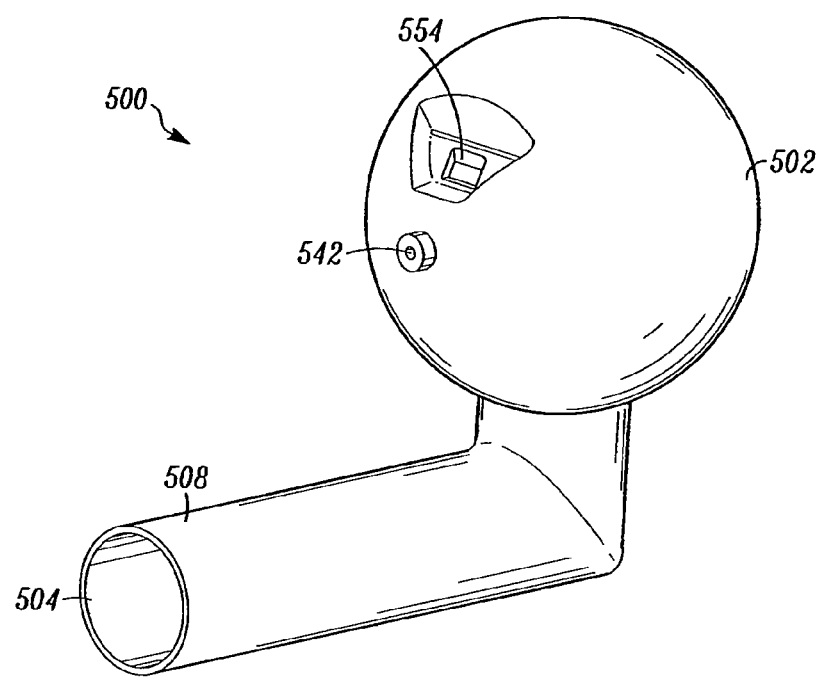
FIG. 26 is a perspective view of a fifth embodiment of an OPEP device.
Figure 27:
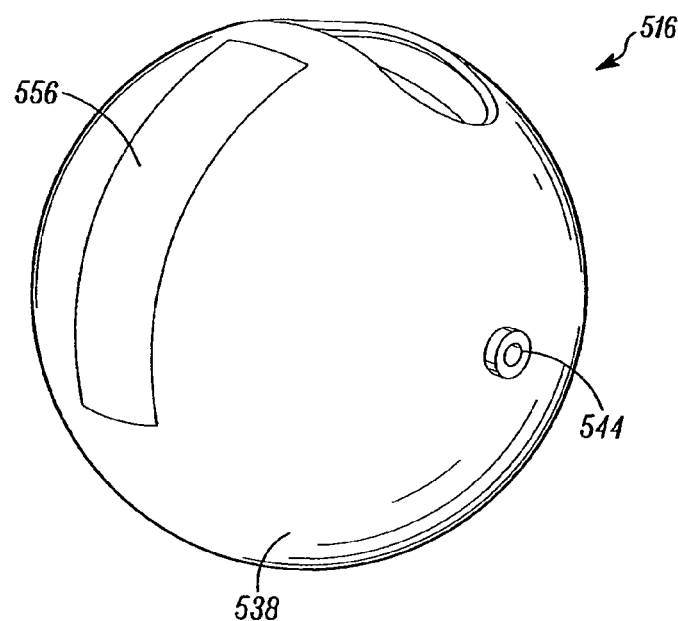
FIG. 27 is a perspective view of a channel assembly of the OPEP device of FIG. 26, showing an indicia disposed on the channel assembly.
Figure 28:
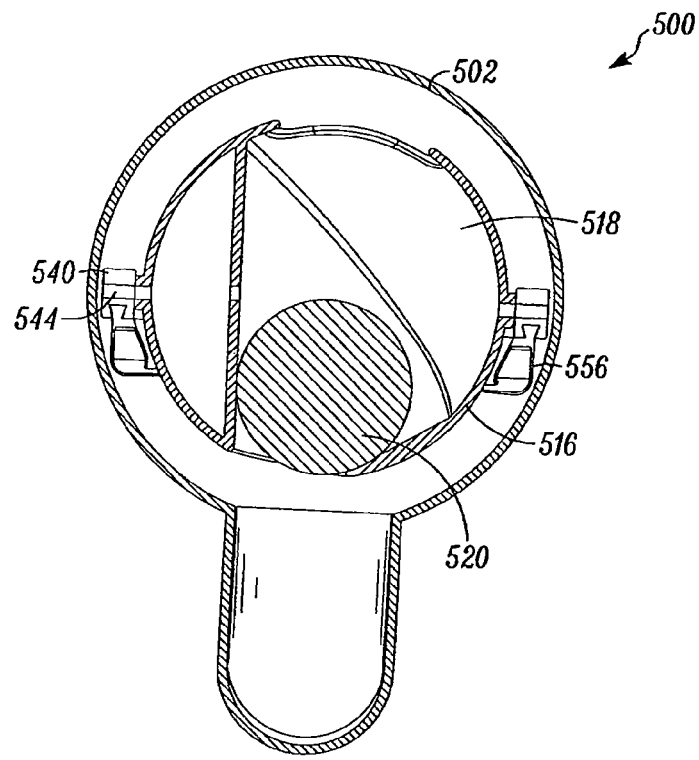
FIG. 28 is a cross-sectional front view of the OPEP device of FIG. 26, showing a flexible annulus configured to form a seal between a housing and a channel of the OPEP device.

Referring to FIGS. 26-28, a fifth embodiment of an OPEP device 500 is shown. In general, the OPEP device 500 comprises a housing 502, a chamber inlet 504, a chamber outlet (not shown), and a mouthpiece 508. The OPEP device 500 further includes a window 554 for viewing a position of the channel assembly 516 (FIG. 26) relative to the housing 502. Although the window 554 may comprise a plate of transparent plastic or glass, the window could alternatively comprise an opening in the housing 502 and serve as the chamber outlet. Similar to the OPEP device 300, the channel assembly 516 is movable relative to the housing 502 via an outer ring connected to the housing 502 by a first gimbal 542, which as shown in FIG. 26, are partially viewable from the exterior of the housing 502.

Turning to FIG. 27, a perspective view of the channel assembly 516 of the OPEP device 500 is shown. The channel assembly 516 also includes an outer ring 540 (FIG. 23) which has been omitted in FIG. 27 for purposes of illustration. An inner sphere 538 is connected to the outer ring 540 by a second gimbal 544 such that the inner sphere is rotatable relative to the outer ring 540 about an axis defined between the second gimbal 544. Furthermore, as previously explained, the outer ring 540 is rotatable relative to the housing 502 about an axis defined between the first gimbal 542. The inner sphere 538 is therefore rotatable in any direction relative to the housing 502 about a center of rotation (not shown) located at the intersection of the axes defined between the first gimbal 542 and the second gimbal 544.

Also shown in FIG. 27, an indicia 556 is disposed on the channel assembly 516 to provide the user with visual feedback regarding the position of the channel assembly 516 within the housing 502. More specifically, the indicia 556 is disposed on the inner sphere 538 so that it moves with a channel (FIG. 28) of the OPEP device 500. The indicia is positioned on the channel assembly 516 in a location relative to the window 554 such that, as long as the user can view at least a portion of the indicia 556 through the window 554, the OPEP device 500 is in an orientation conducive to providing the prescribed OPEP therapy. Although the indicia 556 is shown as being a rectangular strip, the indicia 556 could be any number of shapes or sizes, depending on various factors influencing the operating parameters, including the shape and size of the air flow regulator and/or the channel 518.

Turning to FIG. 28, a cross sectional front view of the OPEP device 500 is shown. Like the OPEP device 300, a seal in the OPEP device 500 between the channel assembly 516 and the housing 501 helps to effectively provide OPEP therapy. As such, the OPEP device 500 includes a flexible annulus 556 connected to the outer ring 540 and disposed between the housing 502 and the channel assembly 516. The flexible annulus 556 is adapted to expand and form a seal between the housing 502 and the channel assembly 516 in response to an increased pressure generated as a user exhales into the OPEP device 500. In all other aspects, the OPEP device 500 administers OPEP therapy in the same way as described above in relation to the OPEP device 100.

With respect to the embodiment of FIGS. 26-28, it should be appreciated that the range of movement conducive to the administration of OPEP therapy may be limited by the configuration of the housing 502 and/or the location of the chamber outlet. More specifically, the administration of OPEP therapy becomes impossible if the outer ring 540 rotates relative to the housing 502 such that the flexible annulus 556 moves past the chamber outlet, forming an exhalation flow path directly between the chamber inlet and the chamber outlet, i.e., an exhalation flow path that bypasses the channel assembly 516. Furthermore, exhaled air must traverse the channel assembly 516 and exit the chamber in the same manner as in the previously described embodiments; exhaled air may not flow through the channel assembly 516 in reverse order. Accordingly, the indicia 556 may alternatively be positioned to indicate to the user the total range of orientations permissible for the administration of OPEP therapy.

Figure 29:
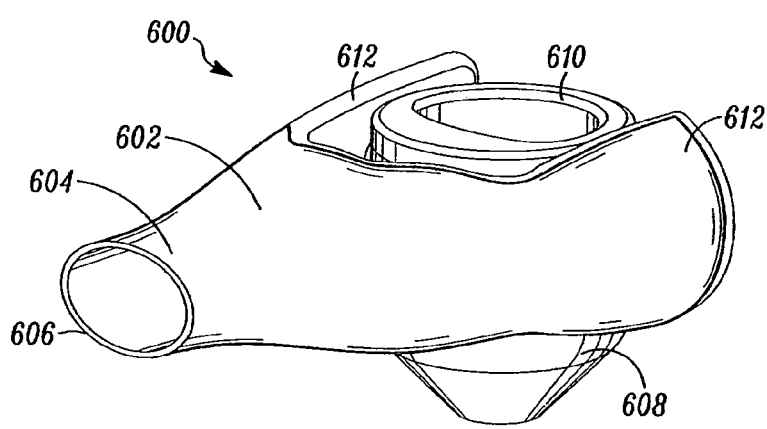
FIG. 29 is a perspective view of a sixth embodiment of an OPEP device.
Figure 30:
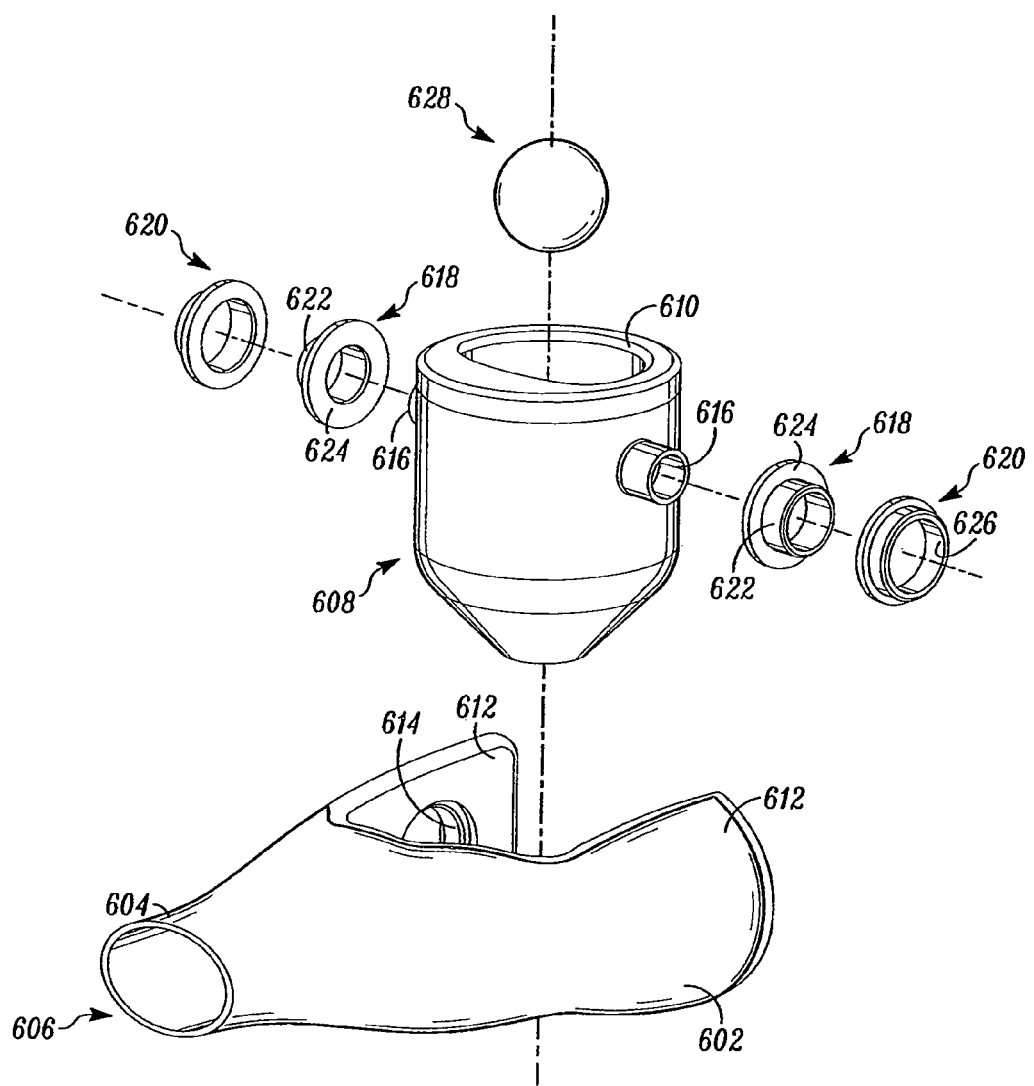
FIG. 30 is an exploded view of the OPEP device of FIG. 29.
Figure 31A:
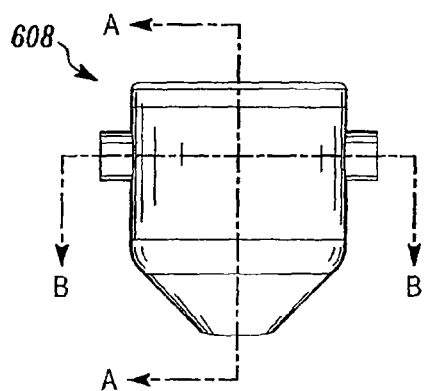
FIGS. 31A-31D illustrates various views of a second housing suitable for use in the OPEP device of FIG. 29.
Figure 31B:
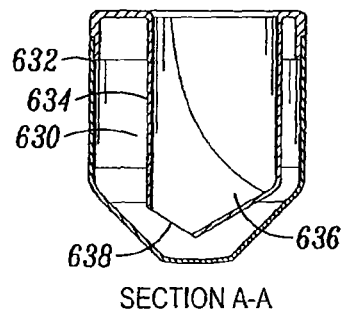
Figure 31C:
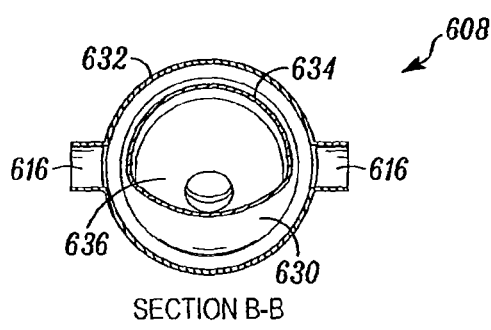
Figure 31D:
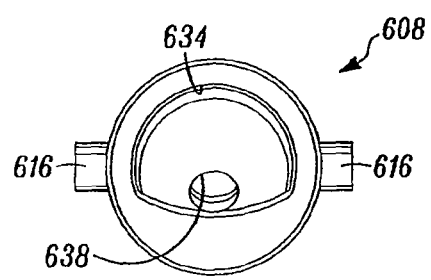

Referring now to FIGS. 29-34, another embodiment of an OPEP device 600 is illustrated. As shown in FIGS. 29-30, the OPEP device 600 includes a first chamber 602 having a mouthpiece 604 defining a chamber inlet 606 for receiving exhaled air, and a second chamber 608 pivotably connected to the first chamber 602 and having a chamber outlet 610. The first chamber 602 is y-shaped and defines a hollow passageway starting at the chamber inlet 606 that splits into two hollow arms 612 that open up into opposing openings 614 on the inside of each of the arms 612. Referring to FIG. 30, a chamber passage 616 extending from each side of the second chamber 608 pivotally connects to the openings 614 in the first chamber 602 using inner and outer bushings 618, 620. Each inner bushing 618 may be press fit onto a respective chamber passage 616 of the second chamber 608 and each outer bushing 620 may be press fit into a respective opening 614 in the first chamber 602. The inner bushing 618 may include an outer surface 622 and a flange 624, where the outer surface 622 is sized to slidably and sealingly fit against the inner surface 626 of the outer bushing 620. The inner and outer bushings 618, 620 may form a fixed seal against the chamber passage 616 and the opening 614, respectively, while the surface between a pair of inner and outer bushings 618, 620 maintains a rotatable seal to permit the second chamber 608 to rotate about the axis defined by the chamber passages 616 with respect to the first chamber 602. In this way, the chamber passages 616, along with the inner and outer bushings 618, 620, function as a gimbal in the same manner as described in relation to other embodiments. An air flow regulator 628, such as the sphere illustrated in FIG. 30, is movably positioned in the second chamber 608 as described in greater detail below.

FIGS. 31A-31D show various views of the second chamber 608. The chamber passages 616 are positioned on opposite sides of the second chamber 608 and provide a means for exhaled air to pass from the first chamber 602 into an outer volume 630 defined between an outer wall 632 and an inner wall 634 of the second chamber 608. The outer volume 630 connects with a channel 636 via an opening 638 defined by the inner wall 634. The outer and inner walls 632, 634, or portions thereof, may have a tapered or roughly conical shape. The overall length of the second chamber 608 may be designed so that the ends of the second chamber 608 clear the base of the y-shaped first chamber 602 such that the second chamber 608 may rotate 360 degrees between the arms 612 of the first chamber 602 about the axis defined by the chamber passages 616. The opening 638 to the channel 636 is sized to cooperate with the air flow regulator 628 as described in greater detail below to create an OPEP. Additionally, the channel 636 may be tapered to bias the air flow regulator 628 toward the opening 638 and automatically maintain an orientation of the second chamber 608 based on the weight of the air flow regulator 628 positioned at the bottom of the channel 636.

Figure 32:
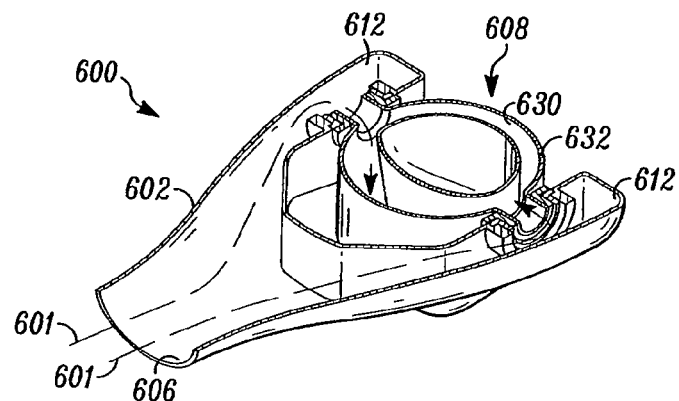
FIG. 32 is a cross-sectional view of the OPEP device of FIG. 29.
Figure 33:
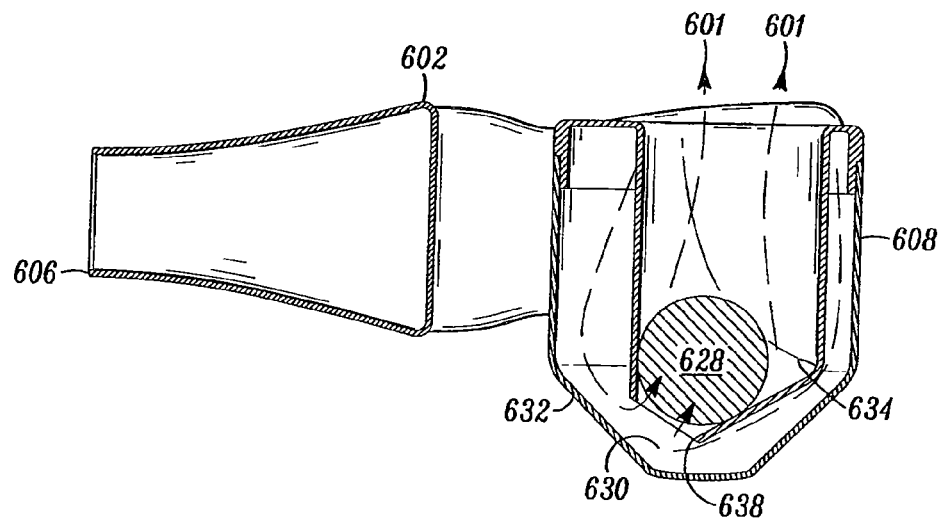
FIG. 33 is a second cross-sectional view of the OPEP device of FIG. 29.

As shown in FIGS. 32-33, the first chamber 602 defines a first part of the exhalation flow path 601 that directs air exhaled into the chamber inlet 606 through each of the two arms 612 that are formed in the distal end of the first chamber 602. The exhalation flow path 601 continues through the openings 614 in the first chamber 602, the inner and outer bushings, 618, 620 and the chamber passages 616 of the second chamber 608. As best shown in FIG. 33, exhaled air then enters the outer volume 630 defined by the an outer wall 632 and an inner wall 634 of the second chamber 608.

The outer and inner walls 632, 634 are sealed together at the top end with a continuous wall so that the only exit for air entering the outer volume 630 via the chamber passages 616 is through an opening 638 to the channel 636 and the chamber outlet 610. The general principles of operation for the air flow regulator 628 are the same as in the OPEP embodiments described above. The air flow regulator 628, in a first or resting position as shown in FIG. 33, restricts access of exhaled air to the chamber outlet 610. Depending on the shape and size of the air flow regulator 628 and/or the opening 638, the air flow regulator 628 may restrict some or all of the exhaled air flowing through the opening 638. As the user continues to exhale, the pressure within the outer volume 630 increases. As the pressure increases, the force acting on the portion of the air flow regulator 628 restricting the flow of exhaled air through the opening 638 also increases. The force acting on the air flow regulator 628 continues to increase during exhalation until the force of gravity acting on the air flow regulator 628 is overcome, and the air flow regulator 628 moves away from the opening 638 to a second position in the channel 636.

The air flow regulator 628 may roll, slide, or jump to the second position depending on the combination of weight, shapes and sizes of the air flow regulator 628 and the opening 638. As shown, the air flow regulator 628 comprises a sphere having a certain relative size to the opening 638, however any of a number of shapes, sizes and materials can be used for these elements to achieve a desired response and form of movement. When the pressure of exhaled air overcomes the weight of the air flow regulator 628, the air flow regulator 628 moves to a second position that allows at least a portion of exhaled air (or an increased portion) through the opening 638 and out of the OPEP device 600 via the chamber outlet 610. As a result of the airflow regulator 628 being displaced to the second position and air flow increasing, the pressure in the outer volume 630 begins to drop until the force of gravity acting on the air flow regulator 628 overcomes the force of the exhaled air and the air flow regulator 628 returns to the first position. As described previously, this process repeats itself multiple times so that the air flow regulator 628 may oscillate multiple times during each exhalation and transmit an oscillating pressure back through the device 600 to the user exhaling at the mouthpiece 604.

As with previous embodiments discussed above, the OPEP 600 of FIGS. 29-33 is configured to reduce the effect of the orientation of the OPEP device on the amplitude and oscillation frequency of OPEP therapy provided. The weight of the air flow regulator 628 not only helps to set the oscillation frequency and amplitude, but also assists in maintaining the orientation of the channel 636, and consequently, the second chamber 608. For example, the weight of the air flow regulator 628, in cooperation with the chamber passages 616 and the inner and outer bushings 618, 620 between the first and second chambers 602, 608, acts to automatically maintain the orientation of the longitudinal axis of the second chamber 608 in a position generally parallel with the direction of gravity so that the tapered portion of the channel 636 points in the direction of gravity regardless of the angle of the first chamber 602 with respect to the second chamber 608. In the embodiment shown, the second chamber 608 may freely pivot 360 degrees about the axis defined between the chamber passages 616. In other embodiments, the amount of available rotation may be restricted to be less than 360 degrees.

In alternative implementations of the embodiment of FIGS. 29-33, the OPEP device 600 may include an nebulizer port (not shown) with a one-way inhalation valve that remains sealed during exhalation through the chamber inlet 606 and opens to allow air into the OPEP during inhalation. The inhalation port may be located anywhere on the first chamber 602 or the second chamber 608. The one way valve may be any of a number of known valve types and materials, for example a simple flap of flexible material or a duck-bill valve. Also, if one or more of the openings 614 in the first chamber 602 and chamber passages 616 in the second chamber 608 are fabricated from a slippery material, the inner and outer bushings 618, 620 may be omitted and a pivotable, sealed joint achieved.

Figure 34:
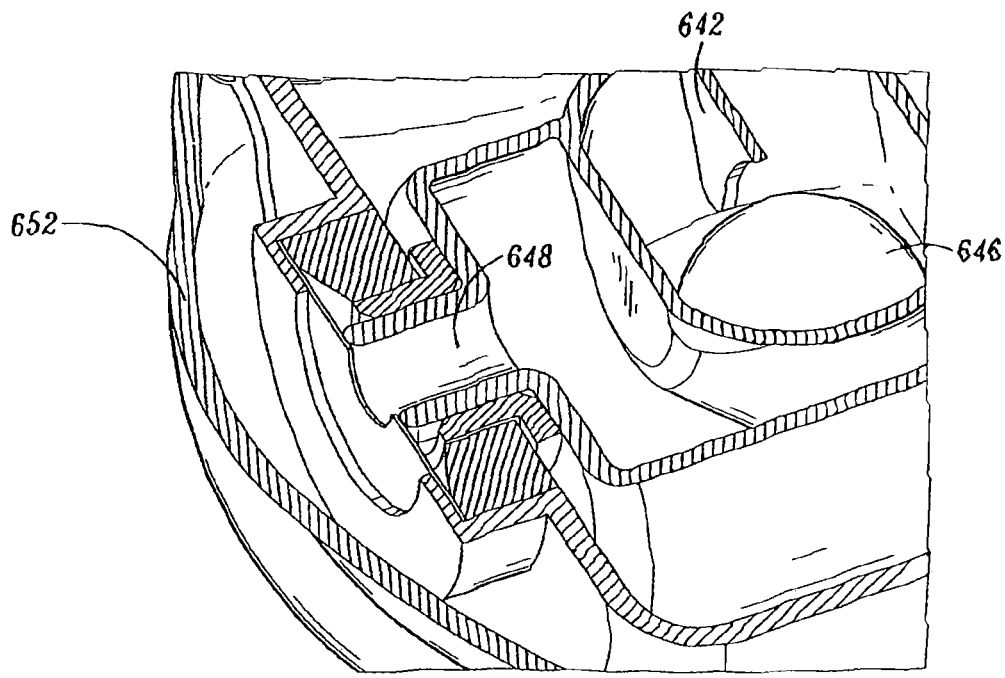
FIG. 34 shows a cross-sectional view of an alternative implementation of the OPEP device of FIG. 29.

Also, as shown in FIG. 34, a fixed or removable air flow regulator retaining member 642 may be located in or on the second chamber 608 to prevent the air flow regulator 628 from being inadvertently removed from the channel 636. The retaining member 642 may be mounted inside the channel 636, for example in the form of one or more protrusions as shown that allow the air flow regulator 628 to move within the channel 636, but prevent it from escaping, or may be a grill or other suitable restraining mechanism fixedly or removably attached to the second chamber 628 over the chamber outlet 610 that lets air escape but prevents the air flow regulator 628 from escaping.

Referring now to FIGS. 35-42, a seventh embodiment of an OPEP device 700 is shown. In general, the OPEP device 700 includes a housing 702 enclosing an chamber 714, a chamber inlet 704, a chamber outlet 706, and a mouthpiece 708. As with previous embodiments, an exhalation flow path, identified by dotted line 711, is defined between the chamber inlet 704 and the chamber outlet 706. The OPEP device 700 also includes an orientation indicator 758 to provide a user with visual feedback of the orientations of the OPEP device 700 suitable for providing OPEP therapy, as explained in greater detail below. In addition, a transparent window 760 may be included with the housing 702 to permit the user to view the components contained therein, such as those that may be adjustable and/or selectively replaced to obtain the desired operating conditions. Like the previous embodiments, it is preferable that the OPEP device 702 is openable, so that the components contained therein are accessible for cleaning, replacement, and/or selective adjustment.

Figure 36:
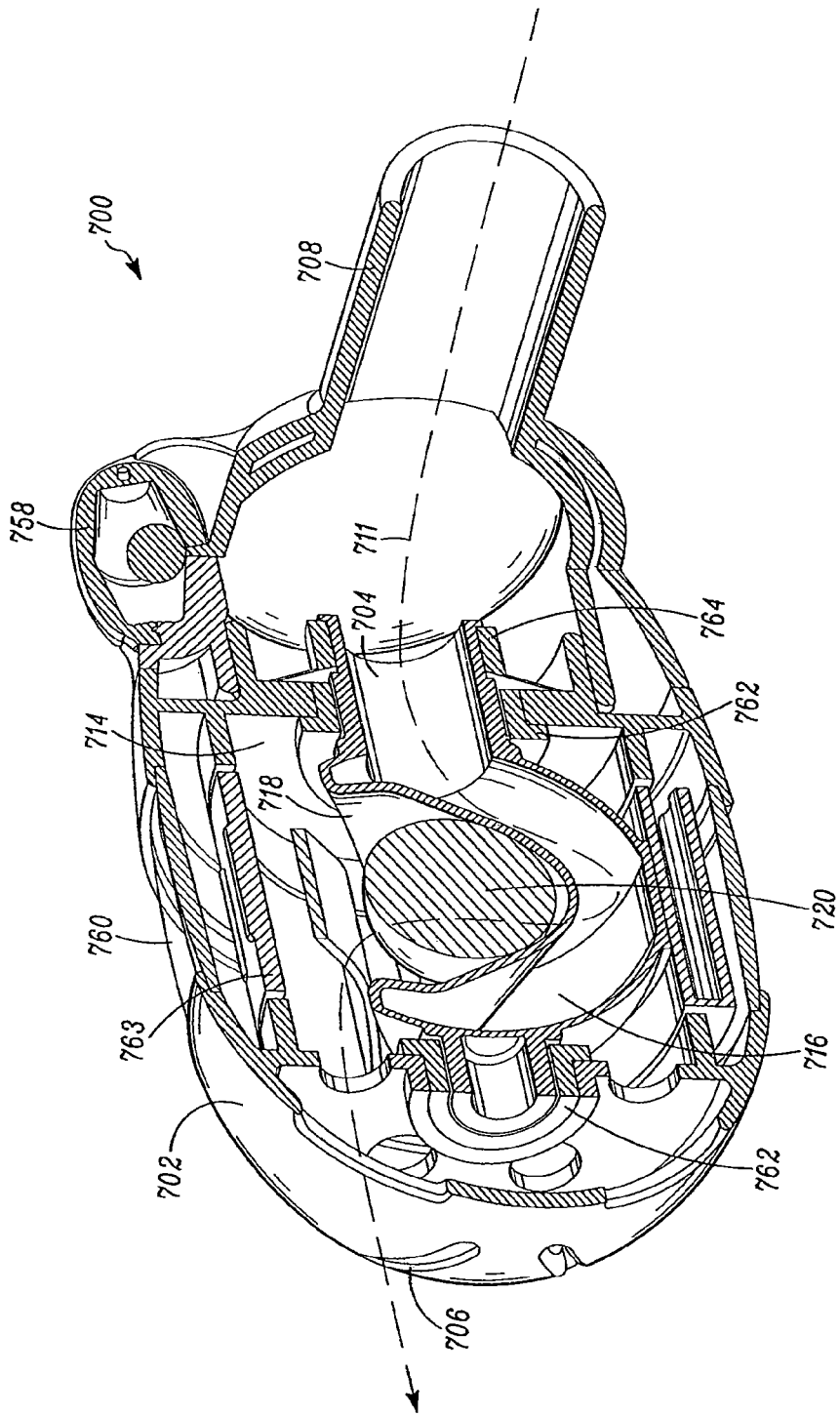
FIG. 36 is a cross-sectional view of the OPEP device of FIG. 35.

Referring to FIG. 36, a cross-sectional view of the OPEP device 700 shows the components housed in the OPEP device 700. As show in FIGS. 36-38, those components include a channel assembly 716, an adjustment band 763, and inner and outer bushings 762, 764, which may operate to seal the chamber 714 and permit the channel assembly 716 to move relative to the chamber 714. As with previous embodiments, the OPEP device 700 also includes an air flow regulator 720 that rests in a channel 718 in the channel assembly 716.

Figure 37:
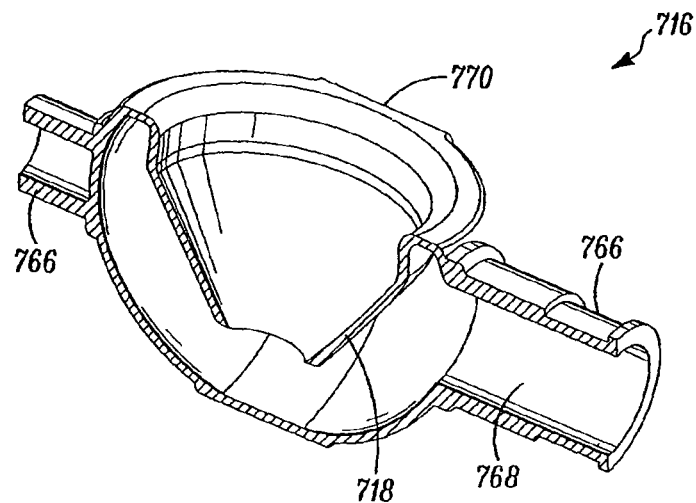
FIG. 37 is a cross-sectional view of a second chamber and of a chamber passage of the OPEP device of FIG. 35.

Turning to FIG. 37, a cross-sectional view of the channel assembly 716 is shown. In addition to the channel 718, the channel assembly 716 comprises a pair of cylindrical supports surfaces 766 about which the channel assembly 716 may be supported by the inner and outer bushings 762, 764 and pivotably attached to the housing 702. In this way, the cylindrical support surfaces act as a gimbal. Furthermore, one of the cylindrical support surfaces 766 forms a passage 768 defining a portion of the exhalation flow path. As shown in FIG. 37, and as previously described in relation to other embodiments, the channel 718 may comprise a truncated cone, the orientation of which may affect the amplitude and frequency of the administered OPEP therapy. Finally, the channel assembly 716 may include an annular surface 770 about which the adjustment band 763 may be mounted.

Figure 38:
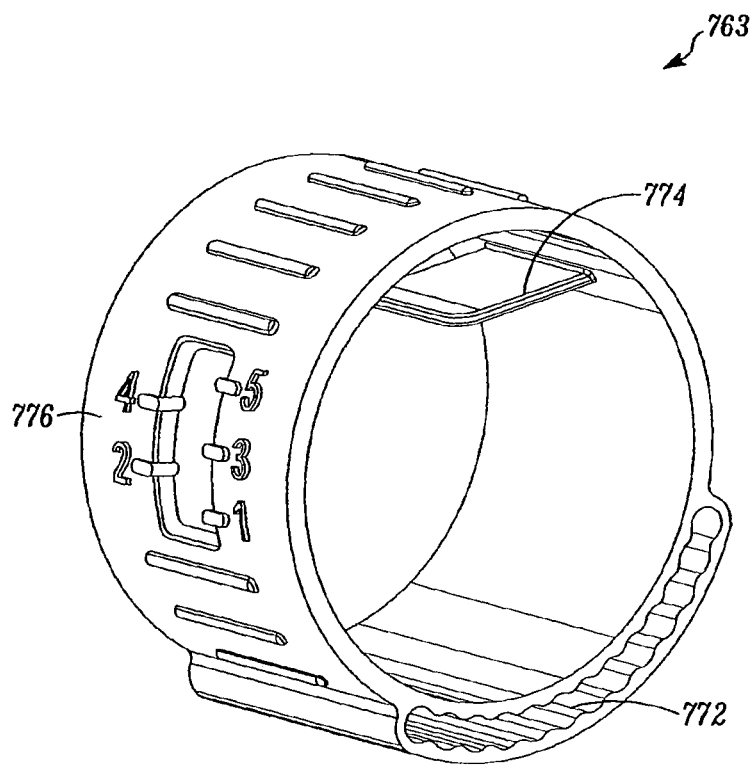
FIG. 38 is a perspective view of an adjustment band of the OPEP device of FIG. 35.

Turning to FIG. 38, the adjustment band 763 of the OPEP device 700 is shown. In general, the adjustment band 763 is shaped and sized to fit around the annual surface 770 of the channel assembly 716 such that the adjustment band 763 and the channel assembly 716 are frictionally engaged with one another, but may be rotated relative to one another under minimal force applied by the user. The adjustment band 763 also includes a secondary weight 772, a retaining member 774 to keep the air flow regulator 720 within the channel 718, and an indicia 776 to show the position of the channel assembly 716 relative to the adjustment band 763. Notably, when the adjustment band 763 is mounted to the channel assembly 716, the position of the secondary weight creates a center of mass offset from the axis about which the channel assembly 716 rotates relative to the housing 702.

Like the previously described embodiments, the OPEP device 700 is adapted to provide OPEP therapy in a variety of orientations. More specifically, as the housing 702 is rotated about the axis defined between the cylindrical support surfaces 766, gravity acting on the secondary weight 772 in the adjustment band 763 causes the channel assembly 716, and thus the channel 718, to rotate relative to the housing 702 to a position where the secondary weight 772 is below the axis between the cylindrical support surfaces 766. In this way, the orientation of the channel assembly 716 will not substantially change as the orientation of the housing 702 is rotated about the axis defined between the cylindrical support surfaces 766. To the extent the orientation of the housing 702 is rotated about the axis perpendicular to the axis defined between the cylindrical support surfaces 766, the orientation indicator 758 provides the user with visual feedback of acceptable orientations for the administration of OPEP therapy, as explained below.

The OPEP device 700 operates in a manner similar to that of the previously described embodiments. As a user exhales into the mouthpiece 708, the exhaled air is forced along the exhalation flow path defined by the dotted line 711. More specifically, the exhaled air is directed through the passage 768 extending into the channel assembly 716. However, the air flow regulator 720, in a first or resting position as shown in FIG. 36, restricts access of exhaled air to the chamber outlet 706. Depending on the shape and size of the air flow regulator 720, the air flow regulator 720 may restrict some or all of the exhaled air flowing through the channel 718. As the user continues to exhale, the pressure behind the air flow regulator 720 increases, and the force acting on the portion of the air flow regulator 720 restricting the flow of exhaled air through the channel 718 also increases. The force acting on the air flow regulator 720 continues to increase during exhalation until the force of gravity acting on the air flow regulator 720 is overcome, and the air flow regulator 720 moves away from its resting position to a second position in the channel 718.

In turn, the increased volume of exhaled air flowing through the channel 718 while the air flow regulator 720 is in the second position results in a decrease in pressure behind the air flow regulator 720. As the pressure decreases, the force acting on the portion of the air flow regulator 720 restricting the flow of air through the channel 718 also decreases until the air flow regulator 720 moves back to the first position under the force of gravity. As this process repeats itself, OPEP therapy is delivered to the user.

The OPEP device 700, like the previously described embodiments, is also selectively adjustable to obtain the desired operating conditions of the OPEP therapy. As previously explained, the oscillation frequency and the amplitude of the OPEP therapy is dependent upon, amongst other variables, the angle of the channel 718 that contacts the air flow regulator 720, the normal force supplied by the channel 718 against the air flow regulator 720, and the direction of gravity relative thereto.

Figure 39C:
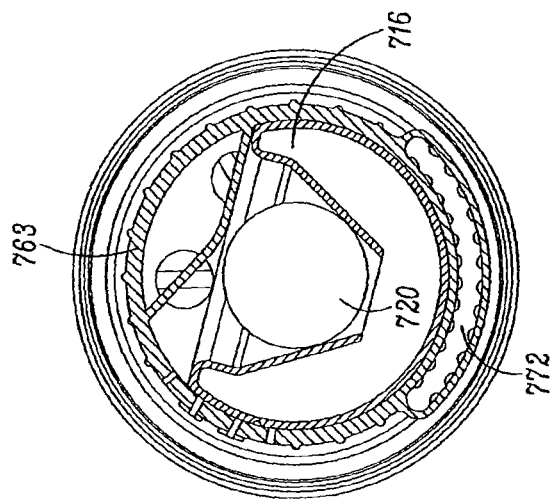
FIGS. 39A-C are cross-sectional side views of the OPEP device of FIG. 35, illustrating movement of the adjustment band of FIG. 38.
Figure 39B:
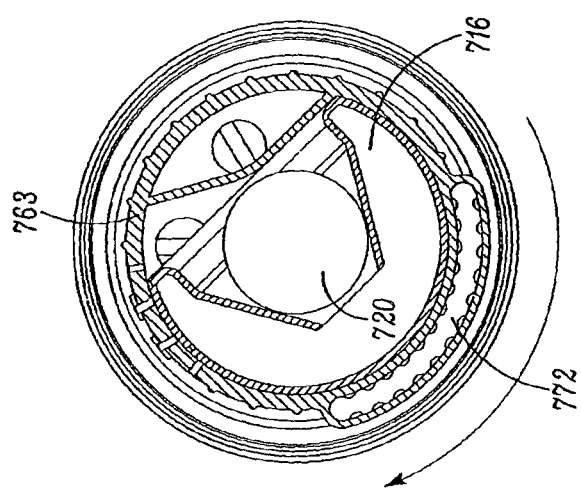
Figure 39A:
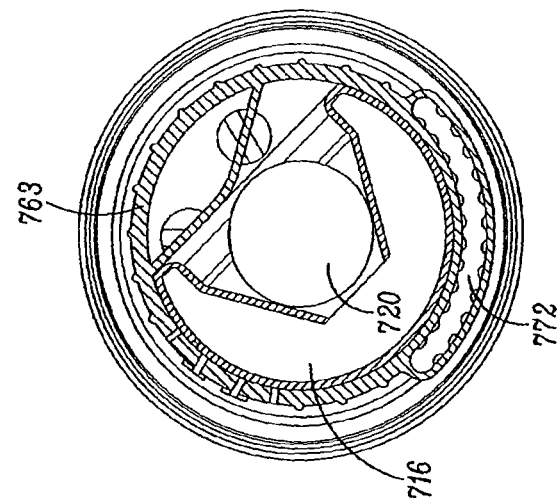

As shown in FIG. 36, the adjustment band 763 and the channel assembly 716 may be frictionally engaged with one another about the annular surface 770 of the channel assembly 716 such that both the channel assembly 716 and the adjustment band 763 are supported by the inner and outer bushings 762, 764 and pivotably attached to the housing 702. Referring to FIGS. 39A-C, an illustration is provided showing the selective rotation of the adjustment band 763 relative to the channel assembly 716. A user may accomplish such an adjustment by opening the housing to access the components contained therein, or by any other suitable means.

Figure 35:
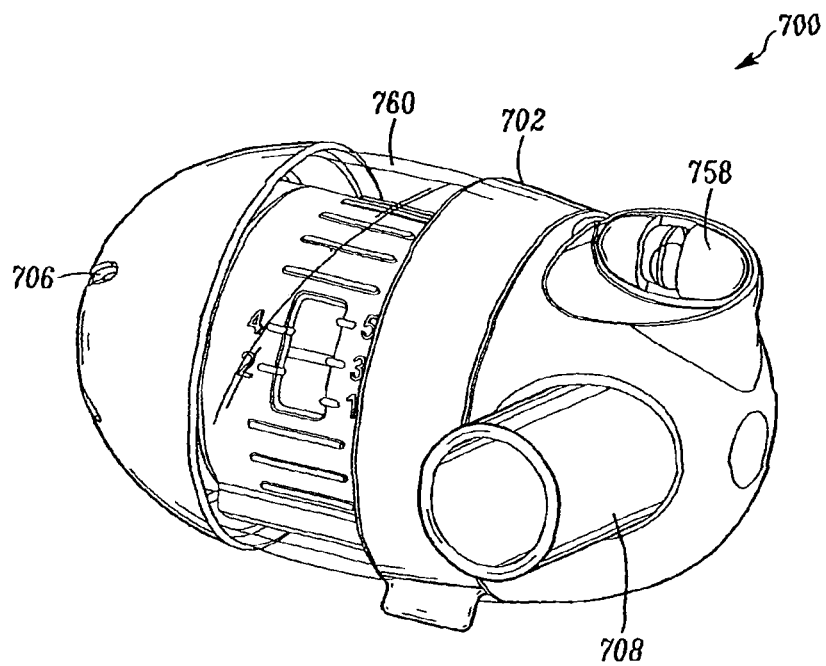
FIG. 35 is a perspective view of a seventh embodiment of an OPEP device.

In FIG. 39A, the channel assembly 716 is shown in one possible orientation relative to the adjustment band 763. Notably, the secondary weight 772 is located below the axis defined between the support surfaces 766 (not shown), as the force of gravity biases the adjustment band 763 and secondary weight 772 to this location. To adjust the frequency and amplitude of the OPEP therapy provided by the OPEP device 700, a user may overcome the frictional engagement between the adjustment band 763 and the channel assembly 716 to rotate the adjustment band 763 relative to the channel assembly 716, as shown in FIG. 39B. Then, as shown in FIG. 39C, once the adjustment band 763 is released and the frictional engagement re-established, the adjustment band 763, and thus the channel assembly 716, will rotate under the force of gravity back to a position where the secondary weight 772 is located under the axis defined between the support surfaces 766. By adjusting the orientation of the channel assembly 716 relative to the adjustment band 763 shown in FIG. 39A to the orientation shown in FIG. 39C, the angle of the channel 718 that contacts the air flow regulator 720, the normal force supplied by the channel 718, and the direction of gravity relative thereto will also have changed. As shown in FIG. 35, such orientations may be viewed by the user through the transparent window 760 included with the housing 702. Furthermore, predetermined orientations may be selected by the user according to the indicia 776 located on the adjustment band 763.

Figure 40:
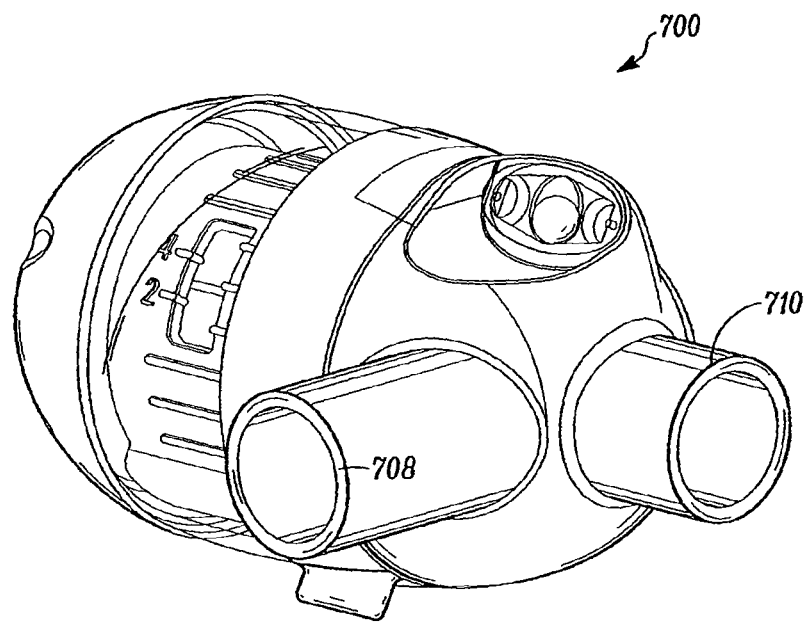
FIG. 40 is a perspective view of the OPEP device of FIG. 35 configured with a nebulizer port for the simultaneous administration of OPEP and aerosol therapies.

Referring now to FIG. 40, the OPEP device 700 may also be adapted to provide simultaneous administration of OPEP and aerosol therapies. As shown, the OPEP device 700 may include a nebulizer port 710 connectable to any number of commercially available nebulizers, such as the one identified above. As described in relation to other embodiments, the nebulizer port 710 may include a one-way valve that remains closed as a user exhales and receives OPEP therapy, but opens upon inhalation to provide the user with aerosol therapy. Notably, and as in the previously described embodiments, the inhalation flow path from the nebulizer port 710 to the mouthpiece 708 bypasses the channel 718, thereby reducing the potential for loss of expensive medicament.

Figure 41:
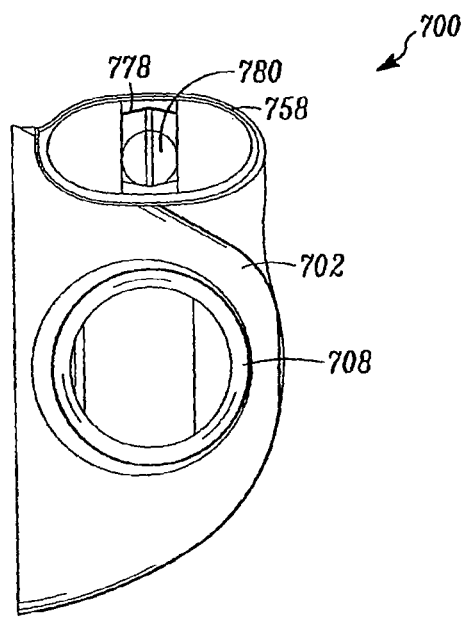
FIG. 41 is a side view of an orientation indicator connected to the OPEP device of FIG. 35.

As illustrated by the various embodiments of the OPEP devices described above, certain OPEP or other respiratory devices may include an orientation indicator to provide a user with visual feedback of the ideal and/or suitable orientation of the OPEP device for the administration of OPEP therapy. By way of example, FIG. 41 shows a portion of the OPEP device 700 with an orientation indicator 758 attached to the housing 702 in a location relative to the mouthpiece 708 such that, as the user exhales into the mouthpiece 708, the user is able view the orientation indicator 758 to determine whether the orientation of the OPEP device 700 is suitable and/or ideal for the administration of OPEP therapy.

In general, the orientation indicator 758 includes a capsule 778 enclosing an indicator 780. The indicator 780 may be comprised of any suitable material, such as a plastic, and may be spherically shaped. The capsule 778 may be shaped, for example, like a pair of cones whose bases are coplanar. Furthermore, the capsule 778 may be connected to the OPEP device 700 such that movement of the OPEP device 700 within a predetermined range of orientations causes the indicator 780 to move to a portion of the capsule 778 near the coplanar bases, thus indicating a suitable and/or ideal orientation of the OPEP device 700 for the administration of OPEP therapy. Likewise, the capsule 778 may be shaped and connected to the OPEP device 758 such that movement of the OPEP device 758 within a separate predetermined range of orientations causes the indicator 780 to move to a portion of the capsule 778 near either tip of one of the pair of cones, thereby indicating an orientation of the OPEP device 700 not suitable or ideal for the administration of OPEP therapy. As a further aid to the user, the orientation indicator 758 may include a form of demarcation identifying the portion of the capsule 778 in which the presence of the indicator 780 indicates an orientation of the OPEP device 700 suitable and/or ideal for the administration of OPEP therapy. In FIG. 41, for example, the demarcation is a non-transparent material surrounding the capsule 778.

Figure 42C:
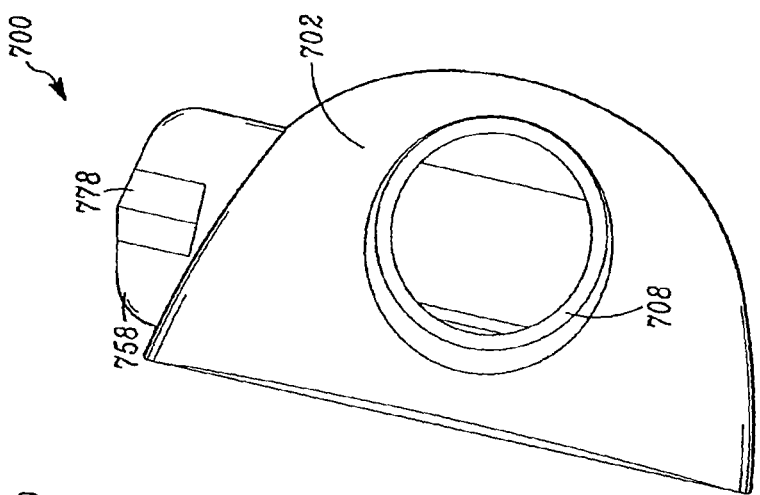
FIGS. 42A-C are side views of the orientation indicator of FIG. 41, illustrating the visual feedback of the orientation indicator for various orientations of the OPEP device.
Figure 42B:
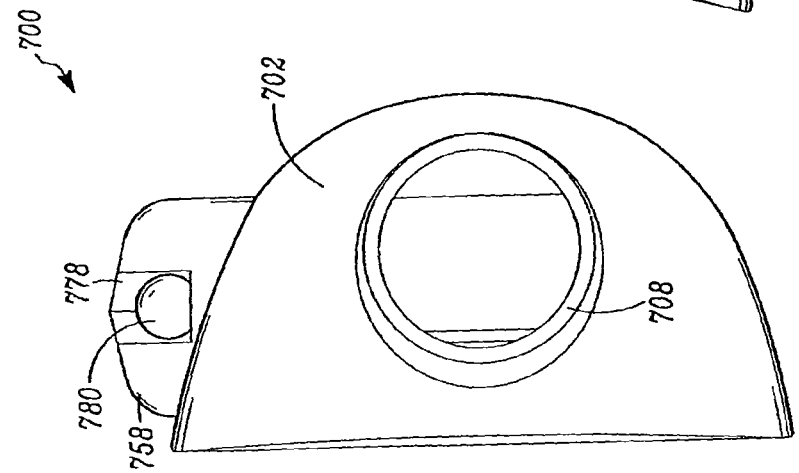
Figure 42A:
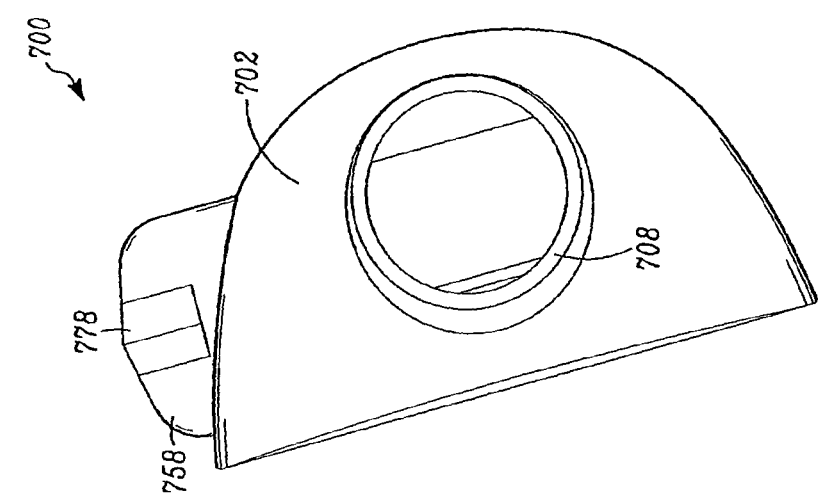

An illustration of the visual feedback provided by the orientation indicator 758 is shown in FIGS. 42A-C. As seen in FIGS. 42A and 42C, when the OPEP device 700 is rotated about the axis perpendicular to the support surfaces (not shown) described above to an orientation not suitable for or ideal to the administration of OPEP therapy, the indicator 780 moves away from the center of the capsule 778 and behind the non-transparent material surrounding the capsule 778. In contrast, while the OPEP device 700 is maintained in an orientation suitable and/or ideal for the administration of OPEP therapy, the indicator 780 remains in the center portion of the capsule 778, as shown in FIG. 42B. In this way, the orientation indicator 758 provides the user with visual feedback of orientations of the OPEP device 700 suitable and/or ideal for the administration of OPEP therapy.

Referring now to FIGS. 43-46, an eighth embodiment of an OPEP device 800 is shown. In general, the OPEP device 800 includes a housing 802 enclosing a chamber 814, a chamber inlet 804, a chamber outlet 806, and a mouthpiece 808. As in prior embodiments, an exhalation flow path, identified by dotted line 811, is defined between the chamber inlet 804 and the chamber outlet 806. The OPEP device 800 also comprises an air flow regulator 820 maintained within a channel 818 extending into the chamber 814.

Figure 45:
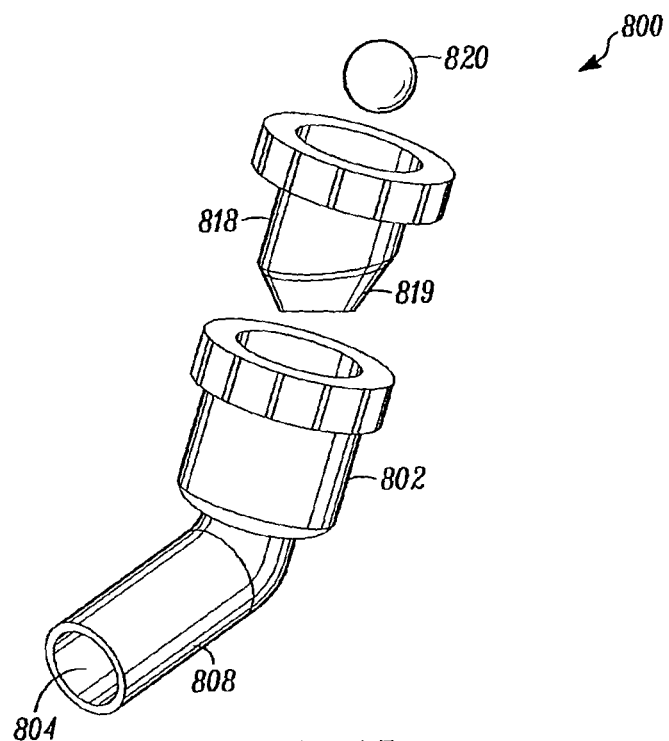
FIG. 45 is an exploded view of the OPEP device of FIG. 43.
Figure 46:
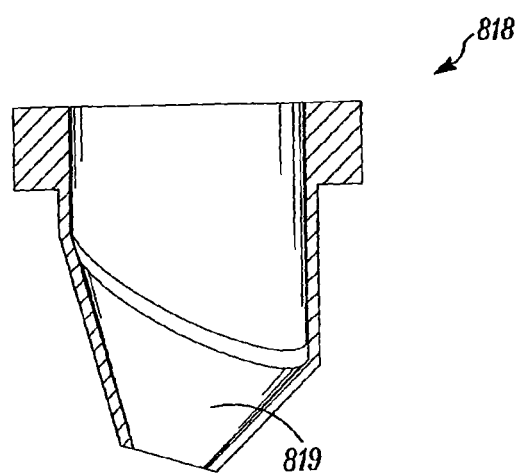
FIG. 46 is a cross sectional side view of a channel of the OPEP device of FIG. 43.

Turning to FIGS. 45-46, the channel 818 of the OPEP device 800 is cylindrically shaped and sized so as to fit within and frictionally engage a corresponding cylindrical portion of the housing 802, thereby forming a seal. As shown and described in relation to prior embodiments, a portion 819 of the channel 818 may comprise a truncated cone. The channel 818 may also include a fixed or removable air flow regulator retaining member (not shown) disposed within the channel 818 so as to keep the air flow regulator 820 within the confines of the channel 818.

The OPEP device 800 operates substantially the same as described above in relation to other embodiments, except that its operation is partially dependent upon the orientation of the OPEP device 800. To that end, the OPEP device 800 may include one or more suitable orientation indicators, such as those described above.

Figure 43:
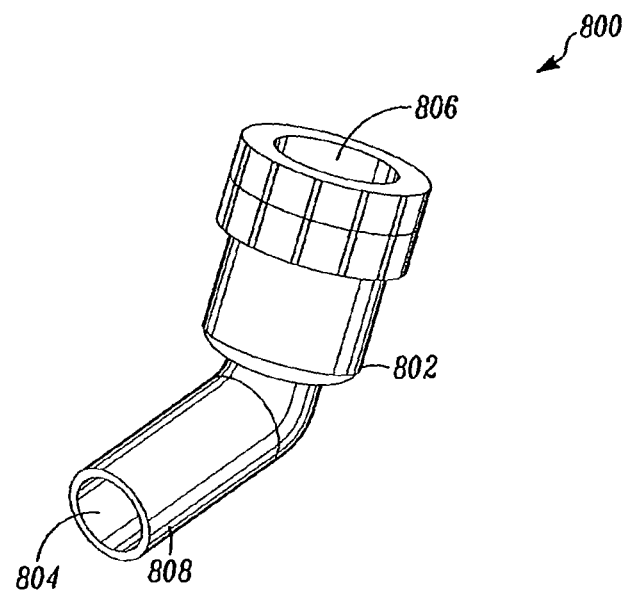
FIG. 43 is a perspective view of an eighth embodiment of an OPEP device.
Figure 44:
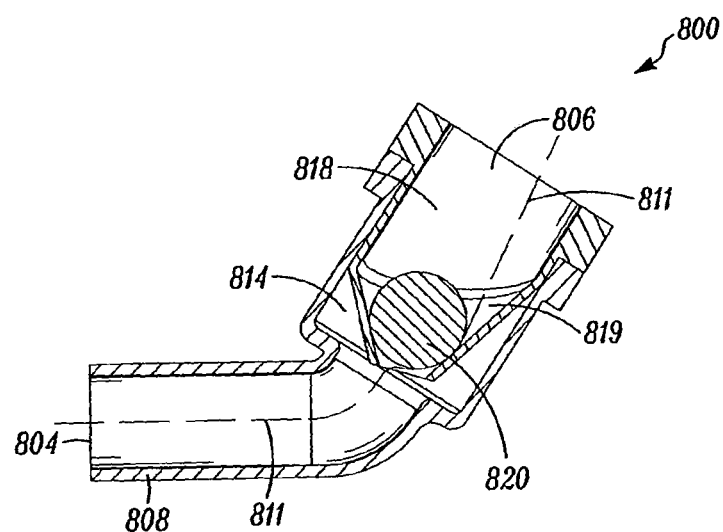
FIG. 44 is a cross-sectional side view of the OPEP device of FIG. 43.

When held in a substantially upright position, as shown in FIG. 43, the air flow regulator will move under the force of gravity to a resting position in the base of the truncated cone, as shown in FIG. 44. As a user exhales into the mouthpiece 808 through the chamber inlet 804, the air flow regulator 820 restricts the flow of air through the channel 818 flowing to the chamber outlet 806, causing the pressure in the chamber 814 to increase. The pressure in the chamber 814 continues to increase until the force acting on the portion of the air flow regulator 820 restricting the flow of air through the channel 818 overcomes the force of gravity acting on the air flow regulator 820, thereby causing it to move away from its resting position to a second position in the channel 818. In the second position, the air flow regulator 820 restricts less air from flowing through the channel 818 to the chamber outlet 816. In turn, the pressure in the chamber 814 decreases and the force of gravity acting on the air flow regulator 820 causes it to return to its first, or resting position. As with previous embodiments, this process repeats itself as the user continues to exhale, effectively transmitting an oscillating back pressure to the user for the administration of OPEP therapy.

The OPEP device 800, although being partially dependent upon the orientation of the OPEP device 800 for the administration of OPEP therapy, is also selectively adjustable by a user. More specifically, the portion 819 of the channel 818 comprising a truncated cone has a central axis offset from the central axis of the cylindrical channel. As such, when a user overcomes the force of friction between the channel 818 and the housing 802 to rotate the channel 818, the user changes the angle of the channel 818 that contacts the air flow regulator 820, the normal force supplied by the channel 818 against the air flow regulator 820, and the direction of gravity relative thereto. As previously explained, these variables affect the resistance of the air flow regulator 820 to the flow of exhaled air traveling through the channel 818, and impact the amplitude and frequency of the OPEP therapy administered to the user.

Figure 47:
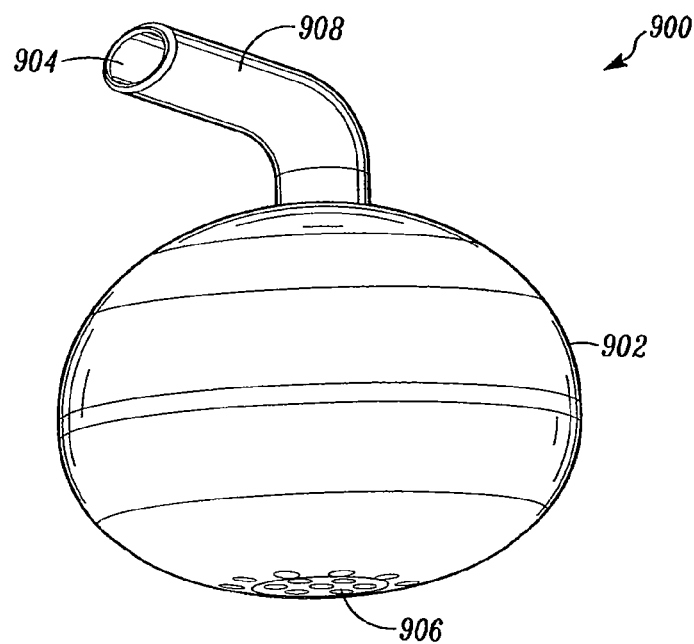
FIG. 47 is a perspective view of a ninth embodiment of an OPEP device.
Figure 48:
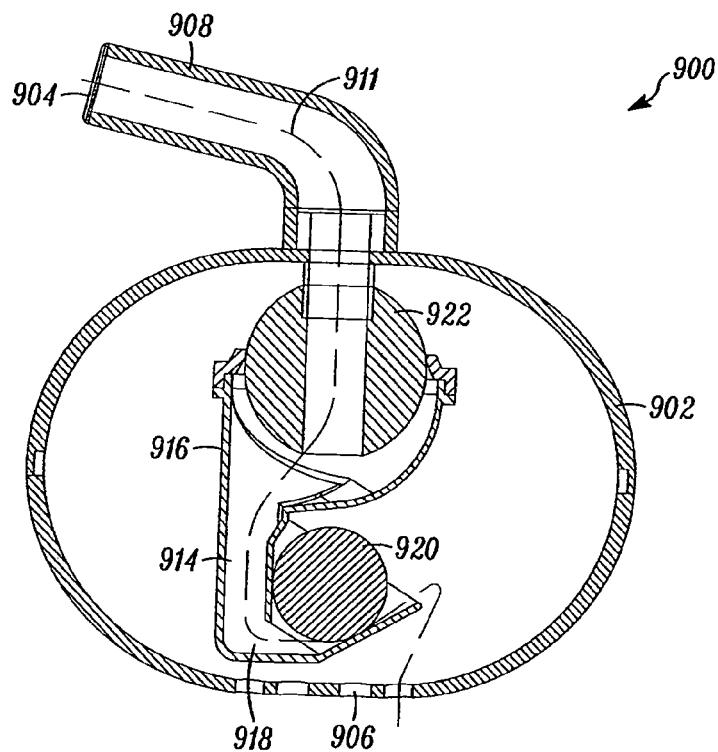
FIG. 48 is a cross-sectional side view of the OPEP device of FIG. 47.
Figure 49:
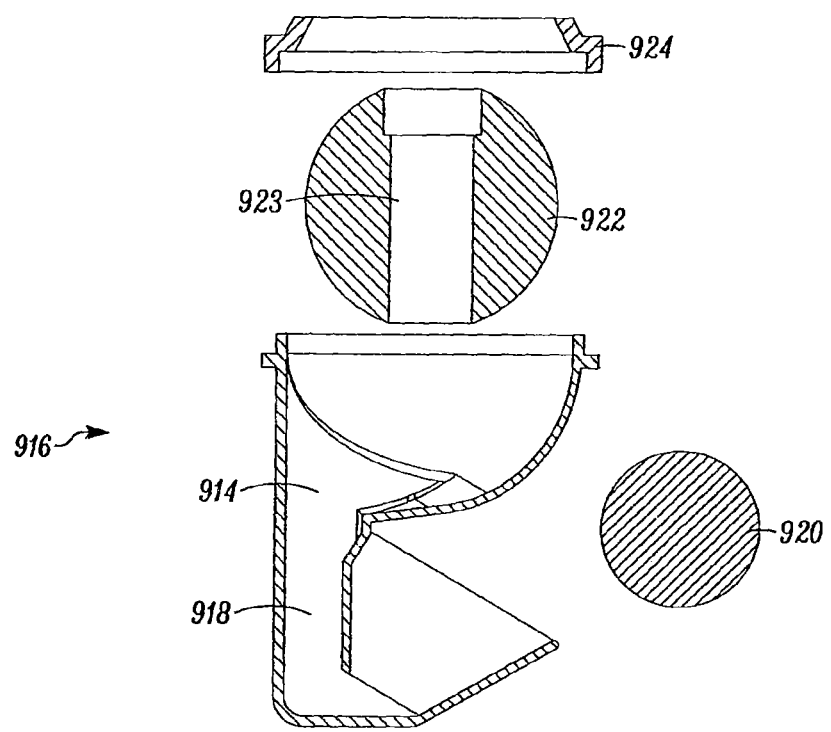
FIG. 49 is an exploded cross-sectional side view of the components housed in the OPEP device of FIG. 47.

Turning now to FIGS. 47-49, a ninth embodiment of an OPEP device 900 is shown. In general, the OPEP device 900 comprises a housing 902, a chamber 914, a chamber inlet 904, a chamber outlet 906, a channel assembly 916, and a mouthpiece 908. An exhalation flow path, identified by dotted line 911, is defined between the chamber inlet 904 and the chamber outlet 906.

Referring to FIG. 49, an exploded cross-sectional side view of the channel assembly 916 of the OPEP device 900 is shown. The channel assembly 916 generally includes a channel 918, an air flow regulator 920, a support ring 924, and a rotation ball 922 having a cylindrical bore 923. As with previous embodiments, a portion of the channel 918 comprises a truncated cone in which the air flow regulator 920 is maintained. Although not shown, an air flow regulator retaining member may be affixed to the channel 918 to keep the air flow regulator 920 within the confines of the channel 918. In this embodiment, the channel 918 and the bore 923 of the rotation ball 922 also define the chamber 914.

As shown in FIG. 48, the rotation ball 922 is fixedly attached to the housing 902 such that the chamber inlet 904 is in fluid communication with the bore 923. A portion of the channel 918 is spherically shaped and sized so that it may be rotatably mounted about the rotation ball 922 over the bore 923 via the support ring 924. The channel 918 and the support ring 924 may be connectable by any suitable means, such as by snap or compression fit, as shown in FIG. 48. To aid in the creation of a seal around the rotation ball 922, yet maintain mobility of the channel 918 relative to the housing 902, the channel 918, the support ring 924, and the rotation ball 922 may be made of suitable low friction materials (e.g., acetyl, nylon, etc.). Alternatively, a lubricant could be applied to the rotation ball 922 and the support ring 924. In this way, a ball and socket joint is formed such that the channel 918 is supported by the rotation ball 922 and movable within the housing 902 about a center of rotation defined by the center of the rotation ball 922. As in prior embodiments, a weight of the air flow regulator 920 and/or a secondary weight biases the channel 918 in the direction of gravity. Thus, as a user of the OPEP device 900 changes the orientation of the housing 902, a suitable orientation of the channel 918 relative to the direction of gravity is maintained for the administration of OPEP therapy.

The OPEP device 900 administers OPEP therapy in the same manner as the previously described embodiments. In general, as a user exhales into the mouthpiece 908 through the chamber inlet 904, exhaled air flows along the exhalation flow path 911 through the bore 923 and into the chamber 914. However, the weight of the air flow regulator 920, along with its size and shape relative to the channel 918, restricts the volume of exhaled air permitted to pass through the channel 918 and exit the chamber 914. As a result, the pressure in the chamber 914 during exhalation increases, until the force acting on the portion of the air flow regulator 920 restricting the flow of air through the channel 918 overcomes the force of gravity. At that point, the air flow regulator 920 moves from its first, or resting position, as shown in FIG. 48, to a second position, where less air is restricted from flowing through the channel 918. In turn, the increase in the flow of exhaled air through the channel 918 causes the pressure in the chamber 914 to decrease. As the pressure decreases, the force of gravity acting on the air flow regulator 920 overcomes the force from the pressure in the chamber 914 acting on the air flow regulator 920, and the air flow regulator 920 returns to its first, or resting position. As a user continues to exhale, this process repeats itself, the pressure in the chamber oscillates, and OPEP therapy is administered to the user.

The foregoing description of the embodiments has been presented for purposes of illustration and description, and is not intended to be exhaustive or to limit the inventions to the precise forms disclosed. It will be apparent to those skilled in the art that the present inventions are susceptible of many variations and modifications coming within the scope of the following claims.

What is claimed is:

1. A respiratory treatment device comprising:
    an inlet configured to receive air into the device;
    an outlet configured to permit air to exit the device;
    a channel positioned in a flow path between the inlet and the outlet, the channel movable relative to a housing by a force of gravity in response to a change in an orientation of the housing;
    an air flow regulator moveable with respect to the channel between a first position where the flow of air through the channel is restricted, and a second position where the flow of air through the channel is less restricted; and,
    indicia movable with the channel;
    wherein when at least a portion of the indicia is viewable by a user, the indicia provides an indication of the suitability of an orientation of the channel for administration of respiratory treatment.

2. The respiratory treatment device of claim 1, further comprising a window formed in the housing, wherein when the orientation of the channel is suitable for administration of respiratory treatment, at least a portion of the indicia is viewable through the window by a user.

3. The respiratory treatment device of claim 1, further comprising a weight movably attached to the channel, wherein a position of the weight relative to the channel is selectively adjustable by the user.

4. The respiratory treatment device of claim 3, wherein selective adjustment of the position of the weight relative to the channel moves the channel relative to the housing.

5. The respiratory treatment device of claim 3, wherein selective adjustment of the position of the weight relative to the channel moves the channel relative to the air flow regulator.

6. The respiratory treatment device of claim 1, wherein an orientation of the channel relative to the housing is selectively adjustable by the user independent of the orientation of the housing.

7. The respiratory treatment device of claim 1, wherein the air flow regulator is biased toward the first position by the force of gravity.

8. A respiratory treatment device comprising:
    an inlet configured to receive air into the device;
    an outlet configured to permit air to exit the device;
    a channel positioned in a flow path between the inlet and the outlet, the channel movable relative to a housing by a force of gravity in response to a change in an orientation of the housing;
    an air flow regulator moveable with respect to the channel between a first position where the flow of air through the channel is restricted, and a second position where the flow of air through the channel is less restricted; and,
    indicia movable with the channel;
    wherein when at least a portion of the indicia is viewable by a user, the indicia provides an indication of the suitability of the orientation of the housing for administration of respiratory treatment.

9. The respiratory treatment device of claim 8, further comprising a window formed in the housing, wherein when the orientation of the housing is suitable for administration of respiratory treatment, at least a portion of the indicia is viewable through the window by a user.

10. The respiratory treatment device of claim 8, further comprising a weight movably attached to the channel, wherein a position of the weight relative to the channel is selectively adjustable by the user.

11. The respiratory treatment device of claim 10, wherein selective adjustment of the position of the weight relative to the channel moves the channel relative to the housing.

12. The respiratory treatment device of claim 10, wherein selective adjustment of the position of the weight relative to the channel moves the channel relative to the air flow regulator.

13. The respiratory treatment device of claim 8, wherein an orientation of the channel relative to the housing is selectively adjustable by the user independent of the orientation of the housing.

14. The respiratory treatment device of claim 8, wherein the air flow regulator is biased toward the first position by the force of gravity.

15. A respiratory treatment device comprising:
    an inlet configured to receive air into the device;
    an outlet configured to permit air to exit the device;
    a channel positioned in a flow path between the inlet and the outlet, the channel movable relative to a housing by a force of gravity in response to a change in an orientation of the housing;
    an air flow regulator moveable with respect to the channel between a first position where the flow of air through the channel is restricted, and a second position where the flow of air through the channel is less restricted; and, indicia movable with the channel;

wherein when at least a portion of the indicia is viewable by a user, the indicia provides an indication of the suitability of an orientation of the channel relative to the housing for administration of respiratory treatment.

16. The respiratory treatment device of claim 15, further comprising a window formed in the housing, wherein when the orientation of the channel relative to the housing is suitable for administration of respiratory treatment, at least a portion of the indicia is viewable through the window by a user.

17. The respiratory treatment device of claim 15, further comprising a weight movably attached to the channel, wherein a position of the weight relative to the channel is selectively adjustable by the user.

18. The respiratory treatment device of claim 17, wherein selective adjustment of the position of the weight relative to the channel moves the channel relative to the housing.

19. The respiratory treatment device of claim 17, wherein selective adjustment of the position of the weight relative to the channel moves the channel relative to the air flow regulator.

20. The respiratory treatment device of claim 15, wherein an orientation of the channel relative to the housing is selectively adjustable by the user independent of an orientation of the housing.

* * * * *